(12) United States Patent
Siclovan et al.

(10) Patent No.: US 7,727,511 B2
(45) Date of Patent: Jun. 1, 2010

(54) AGENTS FOR IMAGING SOLUBLE A-BETA

(75) Inventors: Tiberiu Mircea Siclovan, Rexford, NY (US); Michael Christopher Montalto, Albany, NY (US); Tun Chiao Hubert Lam, Clifton Park, NY (US); Eric Dustin Agdeppa, Fairview, NJ (US); Amy Casey Williams, Clifton Park, NY (US); Cristina Tan Hehir, Niskayuna, NY (US)

(73) Assignee: General Electric Company, Niskayuna, NY (US)

( * ) Notice: Subject to any disclaimer, the term of this patent is extended or adjusted under 35 U.S.C. 154(b) by 742 days.

(21) Appl. No.: 11/609,129

(22) Filed: Dec. 11, 2006

(65) Prior Publication Data

US 2007/0189967 A1 Aug. 16, 2007

Related U.S. Application Data

(63) Continuation-in-part of application No. 10/747,715, filed on Dec. 26, 2003, now abandoned.

(51) Int. Cl.
*A61K 51/00* (2006.01)
*A61M 36/14* (2006.01)

(52) U.S. Cl. .................. 424/1.81; 424/1.11; 424/1.65; 424/1.85; 424/1.89; 549/1; 549/200; 549/400

(58) Field of Classification Search .............. 424/1.11, 424/1.65, 1.81, 1.85, 1.89, 9.1, 9.3, 9.4, 9.5, 424/9.6, 9.7, 9.8; 548/215; 549/200, 1, 400
See application file for complete search history.

(56) References Cited

U.S. PATENT DOCUMENTS

| | | | |
|---|---|---|---|
| 4,560,534 A | 12/1985 | Kung et al. | |
| 5,231,000 A | 7/1993 | Majocha et al. | |
| 5,272,055 A | 12/1993 | Haley | |
| 5,434,050 A | 7/1995 | Maggio et al. | |
| 5,520,904 A | 5/1996 | Nosco et al. | |
| 5,670,634 A | 9/1997 | Marotta et al. | |
| 5,721,130 A | 2/1998 | Seubert et al. | |
| 5,750,349 A | 5/1998 | Suzuki et al. | |
| 5,811,310 A | 9/1998 | Ghanbari et al. | |
| 5,837,672 A | 11/1998 | Schenk et al. | |
| 6,054,114 A | 4/2000 | Lansbury, Jr. et al. | |
| 6,114,133 A | 9/2000 | Seubert et al. | |
| 6,114,175 A | 9/2000 | Klunk et al. | |
| 6,133,259 A | 10/2000 | Klunk et al. | |
| 6,168,776 B1 | 1/2001 | Klunk et al. | |
| 6,274,119 B1 | 8/2001 | Barrio et al. | |
| 6,287,793 B1 | 9/2001 | Schenk et al. | |
| 6,331,440 B1 | 12/2001 | Nordstedt et al. | |
| 6,417,178 B1 | 7/2002 | Klunk et al. | |
| 6,784,180 B2 | 8/2004 | He et al. | |
| 7,166,274 B2 * | 1/2007 | Candau | 424/59 |
| 2002/0159947 A1 | 10/2002 | Zaczek et al. | |
| 2002/0182152 A1 | 12/2002 | Goldstein et al. | |

FOREIGN PATENT DOCUMENTS

| | | |
|---|---|---|
| WO | WO 89/06242 | 7/1989 |
| WO | WO 93/04194 | 3/1993 |
| WO | WO 97/41856 | 11/1997 |
| WO | WO 98/27972 | 7/1998 |
| WO | WO 01/87354 | 11/2001 |

OTHER PUBLICATIONS

Maria M. Piken, "The Changing Concepts of Amyloid", Arh Pathol Lab Med—vol. 125, Jan. 2001, pp. 8-9, 40-43.

Gary W. Small et al., "In Vivo Brain Imaging of Tangle Burden in Humans", Jornal of Molecular Neuroscience, vol. 19, 2002, pp. 323-327.

Chester A. Mathis, et al., "A Lipophilic Thioflavin-T Derivative for Positron Emission Tomography (PET) Imaging of Amyloid in Brain", Biorgaic & Medicinal Chemistry Letters 12, 2002, pp. 295-298.

William E. Klunk et al., "Quantifying Amyloid β-Peptide (Aβ) Aggregation Using the Congo Red-Aβ(CR-AβSpectrophotometric Assay", Analytical Biochemistry 266,, 1999, pp. 66-76.

Chester Mathis et al., "Imaging Technology for Neurodegenerative Diseases", Arch. Neurol., vol. 62, 2005, pp. 196-200.

Nobuyuki Okamura et al., "A Novel Imaging Probe for In Vivo Detection of Neuritic and Diffuse Amyloid Plaques in the Brain", Journal of Molecular Neuroscience, vol. 24, 2004, pp. 247-255.

Margaret Sunde et al., "Common Core Structure of Amyloid Fibrils by Synchrotron X-ray Diffraction", J. Mol. Biol., 1997, 273, pp. 729-739.

Masahiro Ono et al., "Benzofuran Derivatives as Aβ-aggregate-specific Imaging Agents for Alzheimer's Disease", Nuclear Medicine and Biology 29, 2002, pp. 633-642.

Justin Legleiter et al., "Effect of Different Anti-Aβ Antibodies on Aβ Fibrillogenesis as Assessed by Atomic Force Microscopy", J. Mol. Biol. 2004, 335, pp. 997-1006.

S. Heckl et al., "Molecular Imaging: Bridging the Gap Between Neuroradiology and Neurohistology", Histol..Histopathol, 2004, pp. 651-668.

A.R. Oksengaard et al., "Accuracy of CT Scan Measurements of the Medial Temporal Lobe in Routine Dementia Diagnostics", International Journal of Geriatric Psychiatry, 2003, 18:, pp. 308-312.

(Continued)

*Primary Examiner*—D L Jones
(74) *Attorney, Agent, or Firm*—Eileen W. Gallagher

(57) ABSTRACT

Provided herein are agents that bind to soluble beta-amyloid. Also provided are in vivo and in vitro methods for detecting soluble beta-amyloid in a sample that may include brain tissue.

11 Claims, 9 Drawing Sheets

OTHER PUBLICATIONS

Nobuyuki Okamura et al., "Styrylbenzoxazole Derivatives for In Vivo Imaging of Amyloid Plaques in the Brain", The Journal of Neuroscience, March 10, 2004, 24(10): pp. 2535-2541.

Dimitra G. Georganopoulou et al., "Nanoparticle-based Detection in Cerebral Spinal Fluid of Soluble Pathogenic Biomarker for Alzheimer's Disease", PNAS, Feb. 15, 2005, vol. 102, No. 7, pp. 2273-2276.

Alex E. Roher et al., "β-Amyloid-(1-42) is a Major Component of Cerebrovascular Amyloid Deposits: Implications for the Pathology of Alzheimer Disease", Proc. Natl. Acad. Sci., vol. 90, pp. 10836-10840 (year not provided).

Judianne Davis-Salinas et al., "Amyloid β-Protei n. Aggregation Nullifies Its Pathologic Properties in Cultured Cerebrovascular Smooth Muscle Cells", The Journal of Giological Chemistry, vol. 270, No. 36, Sep. 8, 1995, pp. 20887-20890.

Alex E. Roher et al., "Morphology and Toxicity of Aβ-(1-42) Dimer Derived From Neuritic and Vascular Amyloid Deposits of Alzheimer's Disease", The Journal of Biological Chemistry, vol. 271, No. 343, August 23, 1996, pp. 20631-20635.

G.D. Fasman et al., "Solubilization of β-amyloid-(1-42)-peptide: Reversing the β-sheet Conformation Induced by Aluminum with Silicates", Proc. Natl. Acad. Sci., vol. 92, pp. 369-371, Jan. 1995.

Melvin K. Simmons et al., "A Computational Positron Emission Tomography Simulation Model for Imaging β-Amyloid in Mice", Mol. Imaging Biol., 2005, pp. 69-77.

Caroline Hillbich et al., "Aggregation and Secondary Structure of Synthetic Amyloid βA4 Peptides of Alzheimer's Disease", J. Mol. Biol., 1991, 218, pp. 149-163.

Dafang Wu et al., "Drug Targeting of a Peptide Radiopharmaceutical Through the Primate Blood-Brain Barrier in Vivo With a Monoclonal Antibody to the Human Insulin Receptor", The American Society for Clinical Investigation, vol. 100, No. 7, Oct. 1997, pp. 1804-1812.

Wen-hong Li, et al, "Mechanistic Studies of a Calcium-Dependent MRI Contrast Agent", Inorganic Chemistry, 2002, 41, pp. 4018-4024.

Jean-Cosme Dodart, et al., "Immunization Reverses Memory Deficits Without Reducing Brain Aβ Burden in Alzheimer'S Disease Model", Nature Neuroscience, vol. 5, No. 5, May 2002, pp. 452- 457.

Dominic M. Walsh, et al., "Naturally Secreted Oligomers of Amyloid βProtein Potentlyshibit Hippocampal Long-Term Potentiation in vivo", Nature, Apr. 4, 2001, vol. 416, pp. 535-539.

Ronald B. DeMattos, et al, "Brain to Plasma Amyloid-β Efflux: a Measure of Brain Amyloid Burden in A Mouse Model of Alzheimer's Disease", Science, Mar. 22, 2002, vol. 295, pp. 2264-2267.

Jongmin Kang, et al., "The Amide Derivatives of Chrysamine G Protect Human Astrocyte Cells Against Aβ-Induced Toxicity", Bulletin of the Korean Chemical Society, Mar. 20, 2002, vol. 23, No. 3, pp. 363-364,.

Nancy A. Dezutter, et al., "$^{99m}$Tc-Mama-Chrysamine G, A Probe for Beta-Amyloid Protein of Alzheimer's Disease", European Journal of Nuclear Medicine, 1999, vol. 26, No. 11, pp. 1392-1399.

Jongmin Kang, et aL, "The Amide Derivates of Chrysamine G Bind to the β-Amyloid Fibril", Bull. Korean Chem. Soc., 2001, vol. 22, No. 10, pp. 1065-1066.

Rakes Kayed, et al., "Common Structure of Soluble Amyloid Oligomers Implies Common Mechanism of Pathogenesis", Science, Apr. 18, 2003, vol. 300, pp. 486-489.

Ralph Weissleder, et al., "In Vivo Imaging of Tumors With Protease-Activated Near-Infrared Fluorescent Probes", Nature Biotechnology, Apr. 17, 1999, vol. 17, pp. 375-378.

Angelique Y. Louie, et aL, "In Vivo Visualization of Gene Expression Using Magnetic Resonance Imaging", Nature Biotechnology, Mar. 2000, vol. 18, pp. 321-325.

Wolf, Christman, Fowler, Lambrecht, "Synthesis of Radiopharmaceuticals and Labeled Compounds Using Short-Lived Isotopes", Symposium on New Developments in Radiopharmaceuticals and Labeled Compounds, vol. 1, p. 345-381 Copenhagen (1973).

Database Crossfire, Beilstein Institute for Organic Chemistry, Frankfurt-Main, DE; XP002300651, Database accession No. BRN:169730, abstract & J. Amer. Chem. Soc., vol. 96, 1974, pp. 5495-5508.

Database Crossfire, Beilstein Institute for Organic Chemistry, Frankfurt-Main, DE; XP002300652, Database accession No. BRN:5510834, abstract & J. Amer. Chem. Soc., vol. 51, No. 25, 1986, pp. 5040-5041.

Database Crossfire, Beilstein Institute for Organic Chemistry, Frankfurt-Main, DE; XP002300653, Database accession No. BRN:3551523, abstract & Bull. Acad. Sci.., vol. 38, No. 3.2, 1989, pp. 579-580.

Maria M. Pi ken, M.D., Ph.D., "The Changing Concepts of Amyloid", Arch Pathol Lab Med., 2001; 125, pp. 8-9, 40-43.

G.W. Small, et al., "In Vivo Brain Imaging of Tangle Burden in Humans", Journal of Molecular Neuroscience, 2002; 19, pp. 323-327. .

C.A. Mathis, et al., "A Lipophilic Thioflavin-T Derivative for Positron Emission Tomography (PET) Imaging of Amyloid in Brain", Bioorganic & Medicinal Chemistry Letters, 2002; 12, pp. 295-298.

W.E. Klunk, et al., "Quantifying Amyloidβ-Peptide (Aβ) Aggregation Using the Congo Red-Aβ(Cr-Aβ) Spectrophotometric Assay", Analytical Biochemistry, 1999; 266, pp. 66-76.

C.A. Mathis, Ph.D., et al., "Imaging Technology for Neurodegenrative Diseases- Progress Toward Detection of Specific Pathologies", Arch neurol, 2005; 62, pp. 196-200.

N. Okamura, et al., "A Novel Imaging Probe for In Vivo Detection of Neuritic and Diffuse Amyloid Plaques in the Brain", Journal of Molecular Neuroscience, 2004; 24, pp. 247-255.

M. Sunde, et al., "Common Core Structure of Amyloid Fibrils by Synchrotron X-ray Diffraction", J. Mol. Biol, 1997; 273, pp. 729-739.

* cited by examiner

AGENTS FOR IMAGING SOLUBLE A-BETA

CROSS-REFERENCE TO RELATED APPLICATIONS

This application is a continuation-in-part of pending U.S. patent application Ser. No.10/747,715, filed Dec. 26, 2003.

FIELD OF THE INVENTION

The present disclosure relates to methods for the detection of soluble beta-amyloid and the measurement of its local concentration in a sample. In some embodiments, the sample may the brain of a subject and the measurement may occur without invasive procedures. The present disclosure also relates to agents that are useful for detecting soluble Beta-Amyloid in either in vitro or in vivo.

BACKGROUND

The main histopathological characteristic of Alzheimer's disease ("AD") is the presence of neuritic plaques and tangles combined with associated inflammation in the brain. It is known that plaques are composed mainly of deposited (or insoluble in aqueous solution) fibrillar forms of the beta-amyloid ("A-beta") peptide. The formation of fully fibrillar aggregated A-beta peptide is a complex process that is initiated by the cleavage of the amyloid precursor protein ("APP"). After cleavage of APP, the monomeric form of A-beta may associate with other monomers, presumably through hydrophobic interactions or domain swapping, to form dimers, trimers and higher-order oligomers. Oligomers of A-beta may further associate to form protofibrils and eventual fibrils, which is the main constituent of neuritic plaques. Soluble oligomers (soluble in aqueous buffer) of A-beta may contribute significantly to neuronal dysfunction. In fact, animal models suggest that simply lowering the amount of soluble A-beta peptide, without affecting the levels of A-beta in plaques, may be sufficient to improve cognitive function.

Presently, the only definitive method of AD diagnosis is postmortem examination of brain for the presence of plaques and tangles. The antemortem diagnosis of AD is difficult, especially during the early stages, as AD symptoms are shared among a spectrum of other dementias. Currently, AD diagnosis is achieved using simple cognitive tests designed to test a patient's mental capacity such as, for example, the ADAS-cog (Alzheimer's disease assessment scale—cognitive subscale) or MMSE (Mini-mental state examination). The subjective nature and inherent patient variability is a major shortcoming of diagnosing AD by such cognitive means. The fact that AD cannot be accurately diagnosed early creates a formidable challenge for pharmaceutical companies that aim to test anti-A-beta drugs as therapy to slow or halt AD pathogenesis. Furthermore, even if AD could be detected early and patients could be treated with A-beta lowering compounds, there is currently no way to know if the therapy is clinically efficacious. Therefore, a significant need exists to develop methods of measuring the soluble A-beta peptide levels locally in the brain.

Diagnosing AD by directly measuring levels of beta-amyloid non-invasively has been attempted by the targeted imaging of senile plaques. This approach fails as a specific measure of soluble A-beta peptide because current A-beta targeted imaging agents are directed at insoluble aggregates that are characteristic of A-beta fibrillar deposits in the brain. Small molecules that specifically bind to insoluble A-beta deposits include, for example, Congo red, Chrysamine G, methoxy-X04, TZDM, [$^{11}$C]6, IMSB, Thioflavin(e) S and T, TZDM, 1-BTA, benzathiozole derivatives, [$^{125}$I]3, BSB, IMSB, styrylbenzene-derivatives, IBOX, benzoxazole derivatives, IMPY, pyridine derivatives, DDNP, FDDNP, FENE, dialkylaminonaphthyl derivatives, and certain benzofuran derivatives (see, e.g., U.S. Pat. Nos. 6,133,259; 6,168,776; and 6,114,175).

Certain nucleic acid sequences have been shown to bind to insoluble senile plaques of A-beta, including mRNA for furin and amyloid precursor protein ("APP").

Peptides also have been developed as imaging agents for insoluble deposits of A-beta and senile plaques. The sequence specific peptides that have been labeled for the purpose of imaging insoluble A-beta includes the labeled A-beta peptide itself, putrescine-gadolinium-A-beta peptide, radiolabeled A-beta, [$^{111}$In]A-beta, [$^{125}$I]A-beta, A-beta labeled with gamma emitting radioisotopes, A-beta-DTPA derivatives, radiolabeled putrescine, and KVLFF-based ligands.

Inhibitors of aggregated A-beta have been suggested to disrupt the formation of these aggregates by interacting with soluble or insoluble fibrils of A-beta. Examples of inhibitors or anti-aggregation agents include peptides of A-beta, KVLFF-based ligands, small molecular weight compounds, carbon nanostructures, rifamycin, IDOX, acridone, benzofuran, and apomorphine. Agents have also been identified that promote A-beta aggregation (e.g., agents such as A-beta42, proteins, metals, small molecular weight compounds, and lipids).

Targeted imaging of plaques may not provide early diagnosis, as large plaque burden is mostly associated with mid-to-late stage disease. Moreover, it has not been shown that current anti-A-beta therapies will affect fibrillar deposits appreciably to detect by imaging techniques at clinically relevant time points.

In vitro measures of A-beta may be specific for soluble A-beta in the cerebral spinal fluid, but lacks the necessary selectivity for local A-beta in the brain that is necessary for direct, accurate assessment of brain levels of soluble A-beta species. To date, the targeted non-invasive measurement and imaging of soluble A-beta peptide species that exist in the central nervous system have not been addressed.

SUMMARY

This disclosure relates a compound having the following Formula I

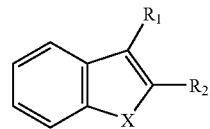

wherein X is selected from a group that comprises at least one of oxygen, nitrogen and sulfur; $R^1$ is selected from the group consisting of substituted or unsubstituted alkyl hydroxy, amide, urea, and urethane; and $R^2$ is a hydrocarbon radical selected from the group consisting of a $C_1$-$C_{32}$ substituted or unsubstituted branched or straight chain alkyl, cycloaliphatic, aryl and heteroaryl, including five membered rings, six member rings, and fused systems thereof.

In another aspect, an imaging agent is described, comprising the compound described in Formula I and a label. In yet another aspect, methods of detecting at least one of A-beta species and amyloidogenic peptides comprising the steps of providing a sample suspected of comprising A-beta species or amyloidogenic peptides, applying an imaging agent comprising a compound described in Formula I, and detecting an amount of imaging agent bound to the at least one of A-beta species and amyloidogenic peptides.

In another aspect, methods of assessing an amyloid-related disease comprising the steps of administering to a subject an imaging agent comprising a compound as described in Formula I and detecting the imaging agent bound to at least one of A-beta species and amyloidogenic peptides.

In yet another aspect, methods of non-invasively assessing the therapeutic efficacy of therapies in a subject are described which include the steps of administering to a subject a first dose of a composition described in Formula I, and non-invasively obtaining a baseline measurement of the imaging agent within the subject, administering to the subject a therapy to be evaluated, administering to the subject a second dose of said composition, non-invasively obtaining a second measurement of the imaging agent within the subject, and comparing the two or more measurements separated in time, wherein an increase or decrease in the amount of the imaging agent present indicates the efficacy of the therapy.

FIGURES

Figure 3:
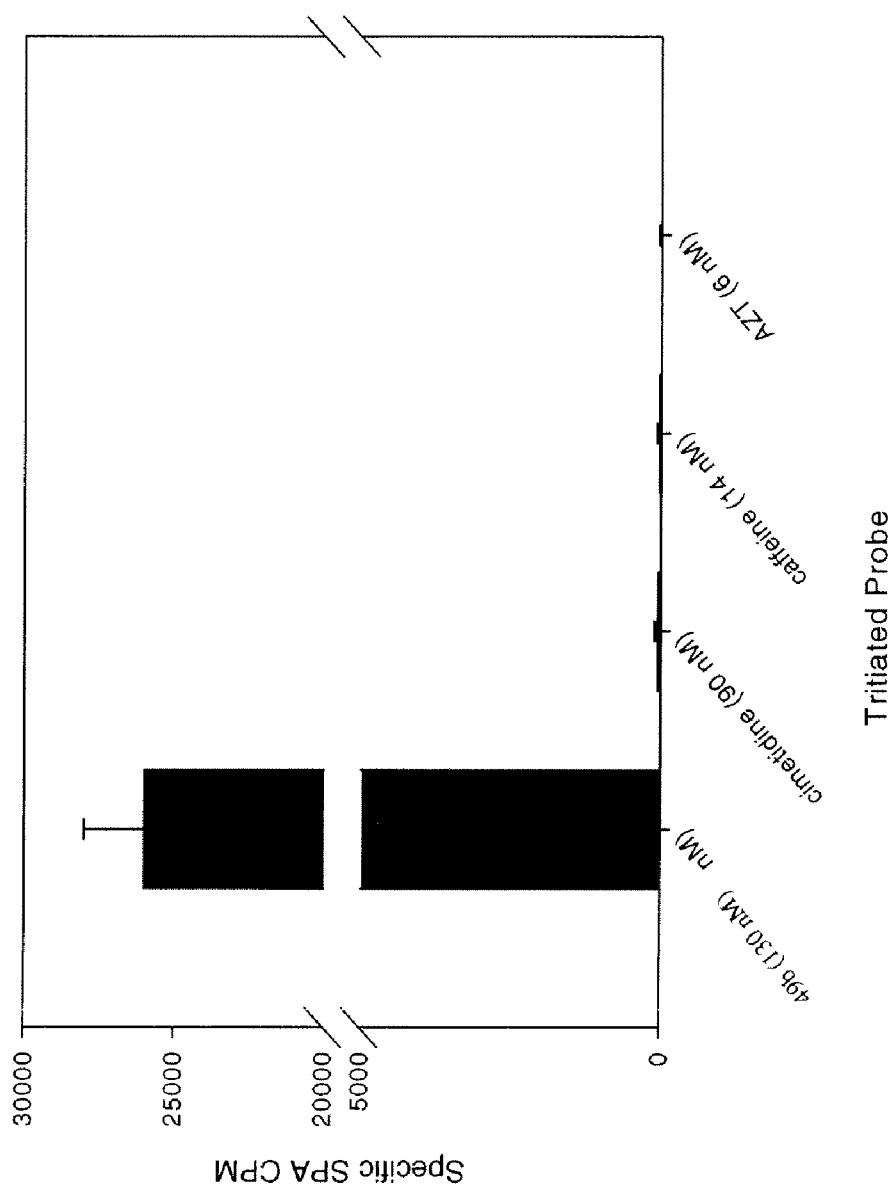

FIG. 3 compares binding of tritiated 49b with other tritiated probes in binding to soluble A-beta oligomers. Tritiated 49b was compared with non-related molecules such as tritiated cimetide, caffeine, and AZT.

Figure 4:
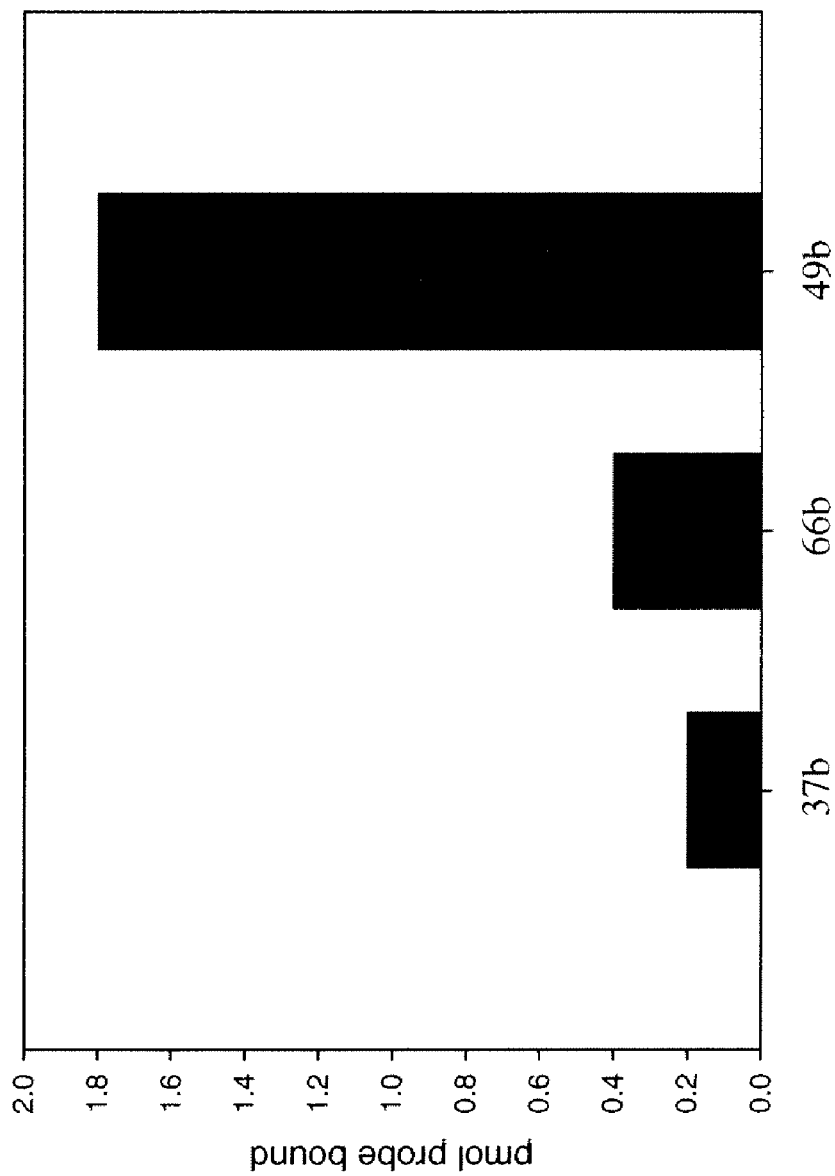

FIG. 4 compares binding of tritiated with related benzofuran analogs 37b and 66b.

Figure 5:
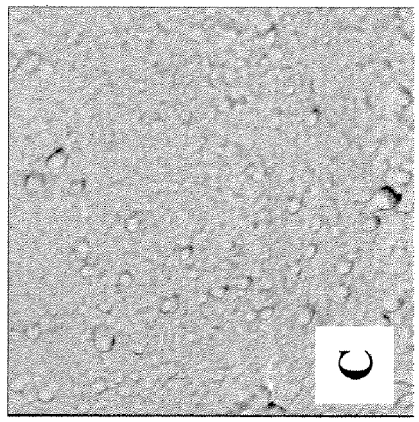
Figure 5:
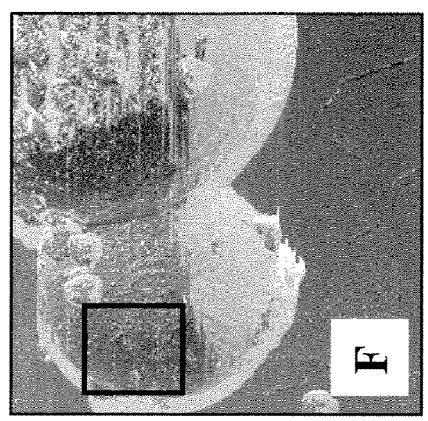
Figure 5:
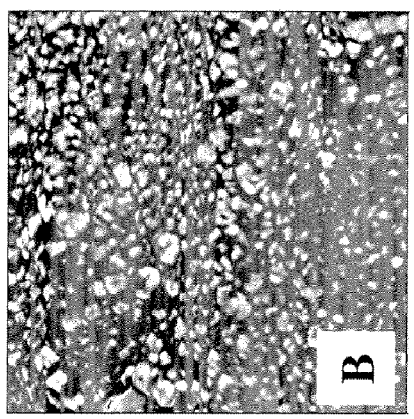
Figure 5:
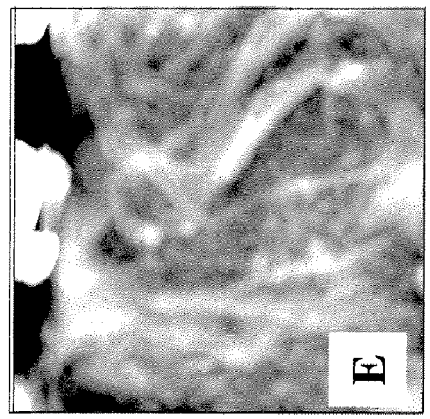
Figure 5:
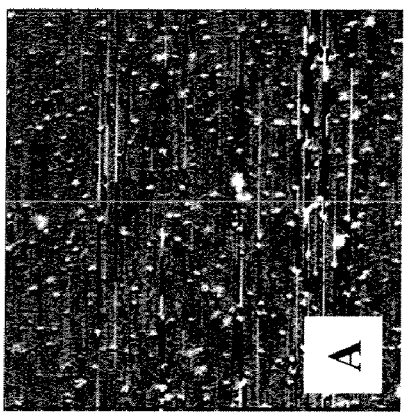
Figure 5:
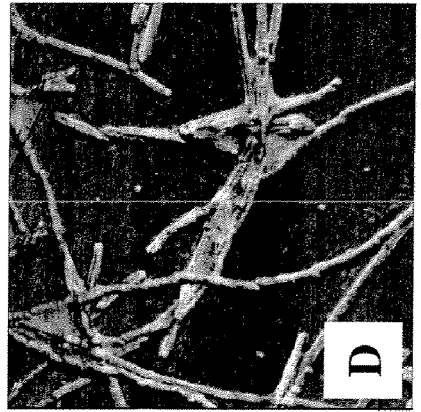

FIG. 5 depicts AFM images of oligomers (Panel A) and fibrils (Panel D) in solution; and oligomers bound to PVT-Streptavidin SPA beads (Panel B) and fibrils (Panels E and F) bound to PVT-Streptavidin SPA beads. The surface of SPA beads alone (without oligomers or fibrils) is shown in Panel C. All images, except the image in Panel F, are 1 um×1 um images. The image shown in Panel E corresponds to the area highlighted by a square in Panel F. Panel E is a topographical image, while all the rest are phase images.

Figure 6:
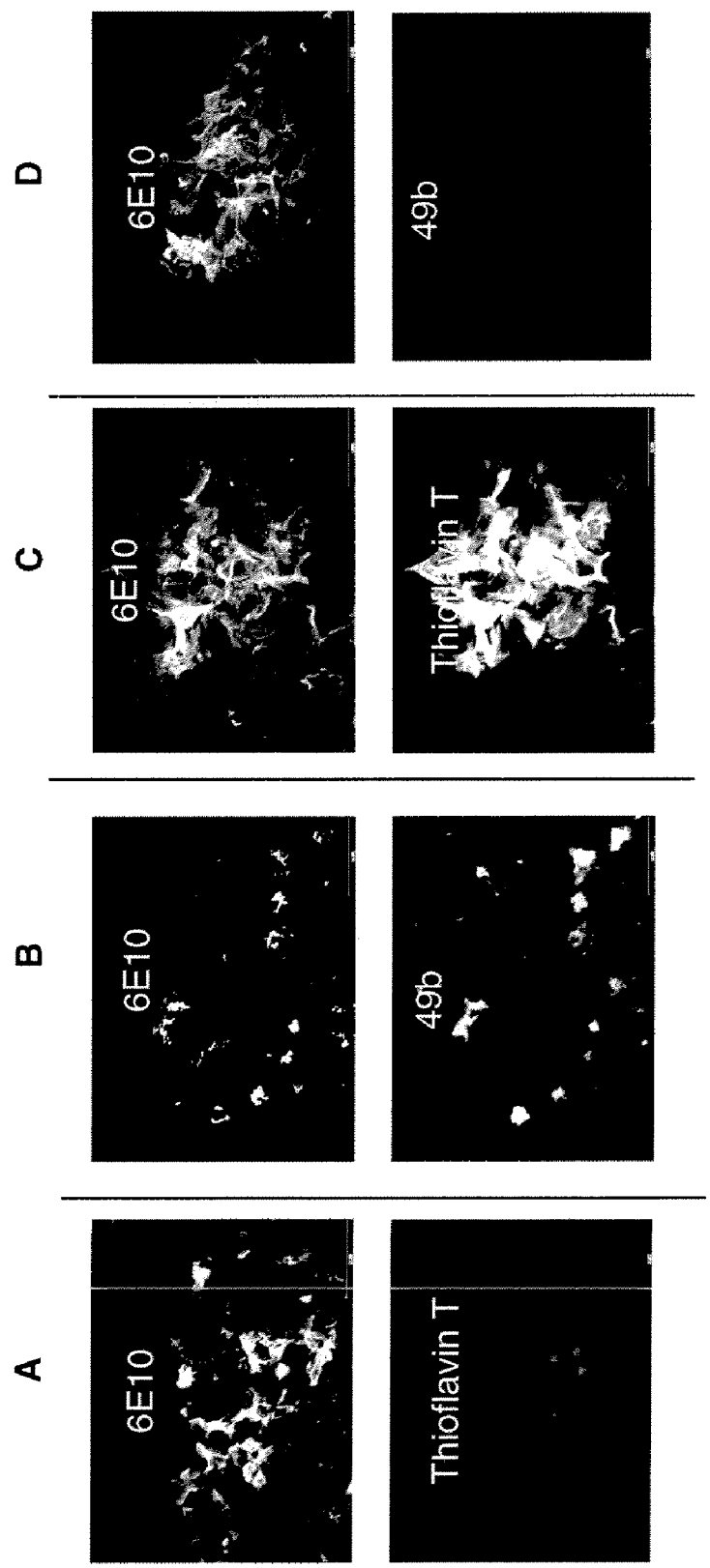

FIG. 6 shows binding of the 49b to synthetic A-beta oligomers in the context of a rat brain slice (Panels A and B), fibrils (Panels C and D). 6E10 immunostaining of the sections were in the top panels (A-D). In Panels A and C, Thioflavin T was used to check for presence of crossed beta-sheets in the synthetic preparations (bottom). In Panels B and D, the slides were exposed to 49b (bottom)

Figure 7:
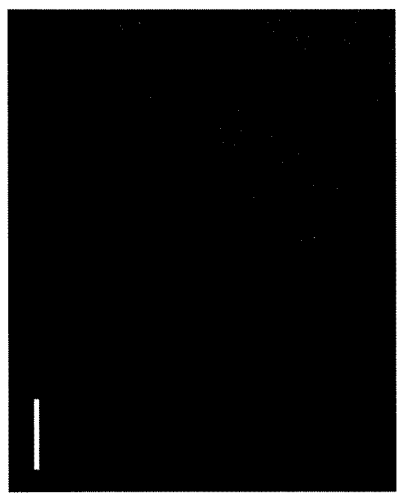
Figure 7:
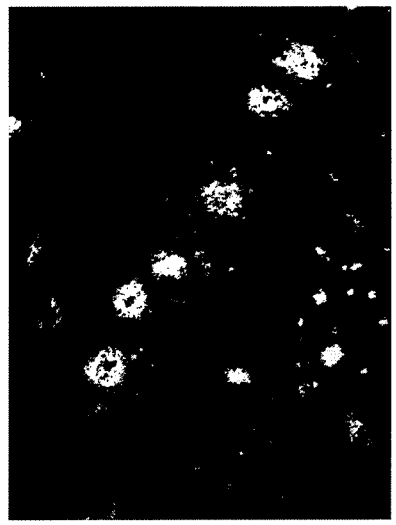
Figure 7:

FIG. 7 demonstrates co-localization of 6E10 antibody with the benzofuran derivative, 49b. Panel A and B show serial staining of brain sample derived from 24-month old PDAPP transgenic mice. Panel C shows the same serial staining in a control animal, which is a 3 month old PDAPP transgenic mice (Panel C). The scale bar in C is 50 microns.

Figure 8:
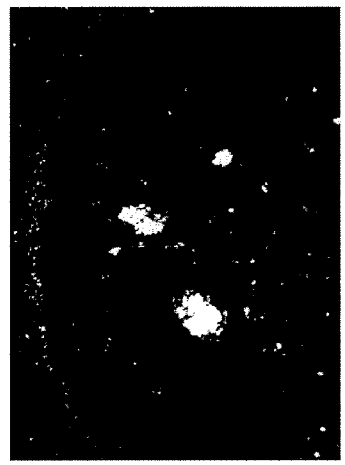
Figure 8:
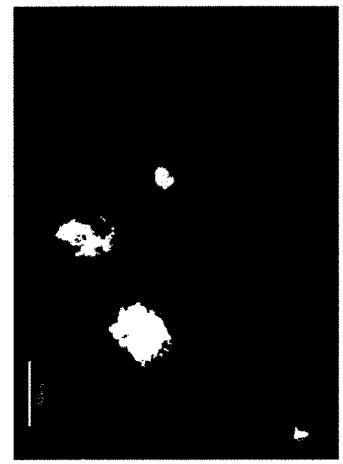
Figure 8:
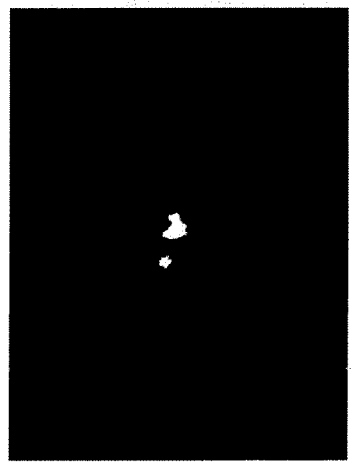
Figure 8:

FIG. 8 shows 49b staining in 24-month old PDAPP co-localized with Thioflavin S-positive staining from the mouse hippocampal sample. Because 49b and Thioflavin S have similar spectral properties, co-localization was demonstrated by staining the sections first with 49b, then washing the sections to remove the first signal, followed by staining with Thioflavin S. Sections shown in Panels A and B were taken from two different PDAPP mice. The scale bar in Panel B corresponds to 50 microns.

Figure 9:
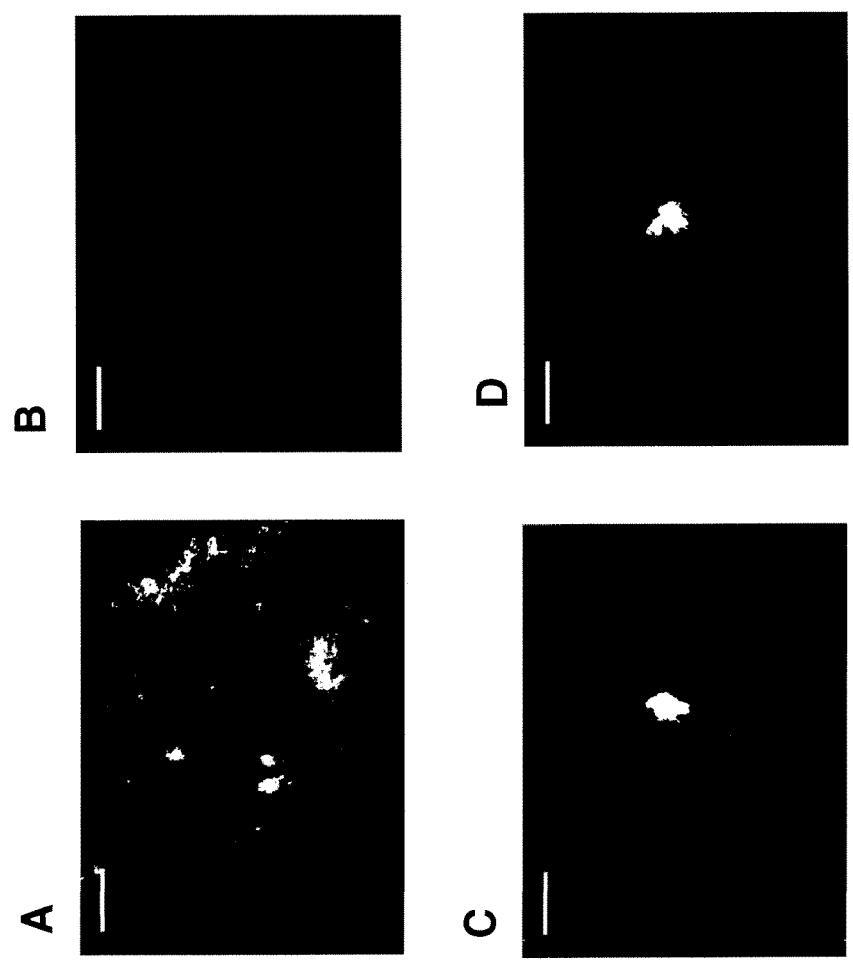

FIG. 9 shows 49b and Thioflavin S binding on 24-month old PDAPP brain sections in which soluble oligomers were removed using carbonate pre-treatment. The samples shown in Panel A and Panel C were pre-treated with PBS, while the samples shown in Panel B and Panel D were pre-treated with carbonate prior to incubation with 49b (Panels A and B), and Thioflavin S (Panels C and D). The scale bar is 50 microns.

DETAILED DESCRIPTION

The following detailed description is exemplary and not intended to limit the invention of the application and uses of the invention. Furthermore, there is no intention to be limited by any theory presented in the preceding background of the invention of the following detailed description of the drawings.

To more clearly and concisely describe and point out the subject matter of the claimed invention, the following definitions are provided for specific terms that are used in the following description and the claims appended hereto.

As used herein, the term "antibody" refers to an immunoglobulin that specifically binds to and is thereby defined as complementary with a particular spatial and polar organization of another molecule. Antibodies useful in present invention may be monoclonal or polyclonal and may be prepared by art-recognized techniques such as immunization of a host and collection of sera (polyclonal) or by preparing continuous hybrid cell lines and collecting the secreted protein (monoclonal), or by cloning and expressing nucleotide sequences or mutagenized versions thereof coding at least for the amino acid sequences required for specific binding of natural antibodies. Antibodies of the various classes and isotypes (e.g., IgA, IgD, IgE, IgG1, IgG2a, IgG2b, IgG3, and IgM) may also include a complete immunoglobulin or functional fragments. In addition, aggregates, polymers, and conjugates of immunoglobulins or their fragments may be used where appropriate so long as an appropriate binding affinity for a particular molecule is maintained.

As used herein, the term "A-beta species" generally refers to the various forms of A-beta-derived polypeptide identified by SEQ ID: 1. In general, A-beta may comprise amyloid polypeptides of varying length, various aggregation states, and/or solubility. The term "A-beta species" is intended to encompass A-beta species of varying polypeptide lengths. Thus, A-beta species may include various forms of A-beta amino acid residues 1 through 43 of the full length A-beta peptide shown in SEQ. ID NO:1. Alternatively, the A-beta species may consist essentially of: residues 1-42 of the full length A-beta peptide, residues 1 through 40 of the full length A-beta peptide, residues 1-39 of the full length A-beta peptide, residues 1-38 of the full length A-beta peptide, residues 3-40 of the full length A-beta peptide, residues 3-42 of the full length A-beta peptide, residues 11-40 of the full length A-beta peptide, residues 11-42 of the full length A-beta peptide, residues 1 7-40 of the full length A-beta peptide, and residues 17-42 of the full length A-beta peptide.

The general term A-beta species also encompasses various forms of A-beta in several aggregation states (e.g., monomeric, soluble oligomers, or insoluble oligomeric). Because a variety of factors may affect which species of A-beta is found in solution, the aggregation state of the A-beta species may be selected according to the user's purposes by altering the A-beta polypeptide length, increasing or decreasing the concentration of A-beta present in a given aliquot of A-beta species, increasing or decreasing the temperature, pH, salt levels and metal content (e.g., $Zn^{2+}$, $Cu^{2+}$, etc.) of the given aliquot of A-beta species.

Various forms of soluble or insoluble A-beta species (regardless of the length of the polypeptide or the association state) may be derived from a variety of mammalian tissue sources, including but not limited to, brain tissue, cerebrospinal fluid, or blood serum. Alternatively, the A-beta species may be synthesized using art-recognized techniques such as protein expression systems or peptide synthesizers.

"Amyloidogenic peptides" as used herein refer to peptides or proteins that have underwent or have the propensity to undergo an amyloidogenic process to form aggregates called amyloid, which have a secondary structure of cross-beta sheets, are birefringent under polarized light, stain with the histological stain Congo red, and are fibrillar in nature.

As used herein the term "complexed" generally refers to the aggregation state of A-beta species in solution (e.g., monomeric or multimeric aggregates of the A-beta polypeptide). Thus, the terms "complex" and "oligomer," as used herein, refer to the polypeptides in the associated or bound state. And, the term "monomer" refers to a single peptide chain of A-beta.

As used herein, the terms "fibrils" and "fibrillar" generally refer to A-beta preparations with largely beta-sheet content that are insoluble aggregates. Fibrils bind Congo Red and Thioflavin T dyes and cause these dyes to produce fluorescence signal. Fibril preparations preferentially comprise substantially fibrillar A-beta, but they may also comprise unsubstantial amounts of globular aggregates.

As used herein, the term "soluble oligomers" generally refers to complexed A-beta polypeptides short chain of monomers derived from the A-beta polypeptide, preferentially less than 25 monomers in length, but may be 100 monomers in length.

As used herein, the term "signal generator" encompasses a substance that is capable of being detected by an imaging modality (e.g., optical detection or radiography) in the course of the disclosed methods. Examples of signal generators include, but are not limited to, fluorophores (e.g., cyanine dyes), radioisotopes, and paramagnetic ions. In some instances, the soluble A-beta binder.

As used herein, the term "small molecule" refers to an organic molecule, either naturally occurring or synthetic, that has a molecular weight less than about 5000 daltons, and preferably in the range of about 200 to about 2000 daltons.

As used herein with regard to the A-beta species, the term "soluble" generally refers to nonaggregated A-beta peptides that are relatively stable and exhibit structural and functional characteristics that are distinct from the fibrillar amyloidogenic form of A-beta. In general the aggregation status of A-beta peptides may be broken into three categories: (1) micelles; (2) protofibrils; and (3) fibrils. The aggregation state of A-beta species may be determined using the techniques set out in Goldsbury et. al, J Struct Biol.; June; 130(2-3):352-62, (2000), in which samples are classified by the amount of β strands in undisturbed solution (pH 7.4 at 37° C.) by circular dichroism. Under these conditions (1) micelles demonstrate 0% β strands; (2) protofibrils demonstrate about 76% β strands; and (3) fibrils demonstrate 100% β strands. Soluble A-beta species for the assays of the invention contain only insubstantial amounts of protofibrils and fibrils.

As used herein, the term "preferentially binds" refers to the specific recognition of one of two different molecules for the other compared to substantially less recognition of other molecules. Thus, an agent that specifically binds a target molecule demonstrates affinities at least five-fold, and preferentially 10-fold to 100-fold affinities greater than non-binders.

Examples of specific binding include antibody-antigen interactions, enzyme-substrate interactions, polynucleotide interactions, and so forth.

An agent exhibits "specific binding" if it reacts or associates more frequently, more rapidly, with greater duration and/or with greater affinity with a particular target (e.g., cells or substances) than it does with alternative targets. The specific binders for a particular A-beta species associates with one or more A-beta species with high affinity for example, an affinity constant of at least $10^7$ $M^{-1}$, preferably between $10^8$ $M^{-1}$ and $10^{10}$ $M^{-1}$, or about $10^9$ $M^{-1}$.

As used herein, the term "species-specific binder" refers to any binder that preferentially attaches to one particular species of A-beta (e.g., soluble A-beta) relative to other species of A-beta (e.g., fibrillar A-beta).

Unless otherwise indicated, all numbers expressing quantities of ingredients, properties such as molecular weight, reaction conditions, so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present invention. At the very least, and not as an attempt to limit the application of the doctrine of equivalents to the scope of the claims, each numerical parameter should at least be construed in light of the number of reported significant digits and by applying ordinary rounding techniques.

Imaging Methods

The present disclosure relates to methods of non-invasively assessing levels of soluble A-beta. Among other uses, the methods disclosed herein may be employed to diagnose or monitor amyloid-related diseases, including AD. In some embodiments, the disclosed methods may be used to qualitatively or quantitatively determine soluble A-beta levels in vivo or ex vivo. In other embodiments, these methods may also be used to determine the efficacy of related therapies used for amyloid-related diseases.

The imaging modality may include positron emission tomography ("PET"), optical, single photon emission computed tomography ("SPECT"), magnetic resonance imaging ("MRI"), ultrasound, computed tomography ("CT"), depending on the label used, the modality available to medical personnel and the medical needs of the subject. Equipment and methods for the foregoing imaging modulations are known to those skilled in the art.

To assess the soluble A-beta levels, a labeled diagnostic imaging agent is delivered to a subject. Typically, the subject is a mammal and may be human. The labeled imaging agent contains at least a chemical entity that binds to soluble A-beta and a chemical entity (e.g., a signal generator) that emits a signal detectable by an imaging modality that is compatible with the signal generator. The labeled imaging agent may be delivered to a subject by a medically appropriate means. After allowing a clearance time according to the label chosen, the amount of imaging agent bound to soluble A-beta is determined by measuring the emitted signal using an imaging modality. The visual and quantitative analyses of the resulting images provide an accurate assessment of the global and local levels of soluble A-beta in the brain.

The present disclosure relates to a method of non-invasively assessing levels of soluble A-beta to diagnose amyloid-related diseases, including Alzheimer's disease. This method qualitatively and quantitatively determines soluble A-beta levels in vivo. This method can also be used to determine the efficacy of related therapies used for amyloid-related diseases. To assess the soluble A-beta levels, a labeled diagnostic imaging agent is delivered to a subject. Typically, the subject is a mammal and can be human. The labeled imaging agent contains at least a chemical entity that binds to soluble A-beta and a chemical entity that emits a signal detectable by an imaging modality. The labeled imaging agent is delivered to a subject by a medically appropriate means. After allowing a clearance time according to the label chosen, the amount of imaging agent bound to soluble A-beta is determined by noninvasively measuring the emitted signal using an imaging modality. The visual and quantitative analyses of the resulting images provide an accurate assessment of the global and local levels of soluble A-beta in the brain.

The present disclosure also relates to a method of labeling and detecting A-beta species and amyloidogenic peptides as well as quantitatively measuring the amount of A-beta species and amyloidogenic peptides in vitro, ex vivo, and in situ. The agent that binds to A-beta species and amyloidogenic peptides is detected by the agent's emitted signal, such as emitted radiation, fluorescence emission, and optical properties of the agent. A-beta species and amyloidogenic peptides from at least cell culture, post-mortem human tissue, animal models of disease, and synthetic and recombinant sources are typically exposed to excess agent for a period of incubation. Agent that is nonspecifically bound or free in the incubation solution is blocked or washed away to leave agent specifically bound to A-beta species and amyloidogenic peptides that is detectable with common microscopic, wide field imaging, radiometric, fluorescent, optical, and analytical techniques. The detectable signal may be converted to numerical values to quantify the amount of targeted A-beta species and amyloidogenic peptides.

The chemical entity of the imaging agent that binds to soluble A-beta can bind to monomers, dimers, trimers, and/or oligomers comprised of a larger number of A-beta peptides up to 24 A-beta peptides. More specifically, the soluble A-beta species to which the imaging agent can bind include monomers, dimers, trimers, and oligomers of A-beta 1-38, A-beta 1-39, A-beta 1-40, A-beta 1-41, A-beta 1-42, A-beta 1-43 or any combination thereof. The A-beta peptide in soluble monomer or oligomer forms can be derived ex vivo, by recombinant means, or synthetically. The soluble A-beta includes monomeric and low oligomeric A-beta that is soluble in an aqueous solution. In some embodiments, the soluble A-beta is of a type that remains in the supernatant of aqueous solution after centrifugation at 15000 times gravity. In some embodiments, the soluble A-beta includes A-beta monomers and its aggregates that do not exhibit green birefringence when stained by Congo red.

The imaging agent that binds to soluble A-beta or otherwise reports on the presence of soluble A-beta can be derived from a natural source or be man made and be a small molecule, peptide, protein, enzyme, nucleic acid, nucleic acid sequence, dendrimer, polymer, antibody or antibody fragment.

As well known in the art, such compounds may be found in compound libraries, combinatorial libraries, natural products libraries, and other similar sources, and may further be obtained by chemical modification of compounds found in those libraries, such as by a process of medicinal chemistry as understood by those skilled in the art, which can be used to produce compounds having desired pharmacological properties.

In one embodiment, certain compounds and their derivatives are useful as imaging agents that bind to soluble A-beta. The compositions described herein exhibit nanomolar affinity to soluble A-beta, as determined by fluorescence binding assays. Suitable compounds and derivatives include those represented by the following Formula I:

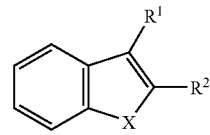

wherein X is selected from a group that comprises at least one of oxygen, nitrogen, or sulfur; $R^1$ is a hydrocarbon radical; and $R^2$ is a hydrocarbon radical or halogen. Preferably, $R^2$ is a hydrocarbon radical. By halogen is meant to include any of the entities known by those of ordinary skill in the art to be halogens, including, but not limited to bromine, fluorine, chlorine, and iodine. By hydrocarbon radical is meant any hydrocarbon radical, including substituted and unsubstituted, saturated or unsaturated, branched, straight chain alkyl, aryl, heteroaryl, cycloalphatic radicals, or any combination of the above. $R^1$ and $R^2$ may further be substituted with one or more heteroatom of oxygen, nitrogen, sulfur, or halogen, such as chlorine, bromine, or fluorine. In one embodiment, $R^1$ is $C_1$-$C_{10}$ alkyl hydroxy, an amide group, a urea group, or a urethane group and $R^2$ is a $C_1$-$C_{32}$ branched or straight chain alkyl, substituted or unsubstituted; a substituted or unsubstituted aryl group; a substituted or unsubstituted cycloaliphatic group.

The term aryl and heteroaryl as used herein is intended to include, but not be limited to, five membered rings, six membered rings and fused ring systems thereof. The term "alkyl" as used in the various embodiments of the present invention is intended to designate both linear alkyl, branched alkyl, aralkyl, cycloalkyl, bicycloalkyl, tricycloalkyl and polycycloalkyl radicals containing carbon and hydrogen atoms, and optionally containing atoms in addition to carbon and hydrogen, for example atoms selected from Groups 15, 16 and 17 of the Periodic Table, including but not limited to oxygen, sulfur, nitrogen, fluorine, bromine and chlorine. The term "alkyl" also encompasses that alkyl portion of alkoxide groups. In various embodiments normal and branched alkyl radicals include as illustrative non-limiting examples $C_1$-$C_{32}$ alkyl optionally substituted with one or more groups selected from $C_1$-$C_{12}$ alkyl, $C_3$-$C_{15}$ cycloalkyl or aryl; and $C_3$-$C_{15}$ cycloalkyl optionally substituted with one or more groups selected from $C_1$-$C_{32}$ alkyl. Some particular illustrative examples comprise methyl, ethyl, n-propyl, isopropyl, n-butyl, sec-butyl, tertiary-butyl, pentyl, neopentyl, hexyl, heptyl, octyl, nonyl, decyl, undecyl, and dodecyl. Some illustrative non-limiting examples of cycloalkyl and bicycloalkyl radicals include cyclobutyl, cyclopentyl, cyclohexyl, methylcyclohexyl, cycloheptyl, bicycloheptyl, and adamantyl. In various embodiments aralkyl radicals are those containing from about 7 to about 14 carbon atoms; these include, but are not limited to, benzyl, phenylbutyl, phenylpropyl, and phenylethyl. In various embodiments aryl radicals used in the various embodiments of the present invention are those substituted or unsubstituted aryl radicals or fused aromatic radicals containing from 6 to 18 carbon atoms. Some illustrative non-limiting examples of these aryl radicals include $C_6$-$C_{15}$ aryl optionally substituted with one or more groups selected from $C_1$-$C_{12}$ alkyl, $C_3$-$C_{15}$ cycloalkyl, or aryl. Some particular illustrative examples of aryl radicals comprise substituted or unsubstituted phenyl, biphenyl, toluyl, and naphthyl.

In yet another embodiment of the present invention, $R^1$ is alkyl hydroxyl, an amide group, a urea group or a urethane group such as those of the following formula:

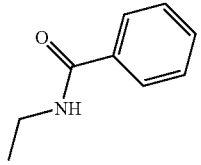 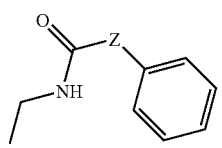

wherein Z is NH or S, or $R^1$ has the following structure

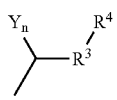

wherein Y is H or O, n is equal to the integer 1 or 2, $R^3$ is O or NH, and $R^4$ is an acyl, substituted or unsubstituted aryl, ureas, or urethanes. Further, nonlimiting examples of $R^2$ include those shown in Table 1 below.

TABLE 1

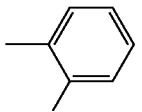
1a

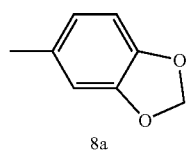
2a

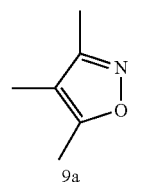
3a

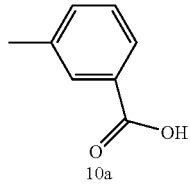
4a

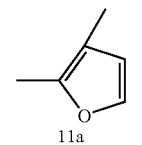
5a

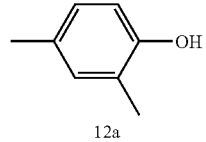
6a

TABLE 1-continued

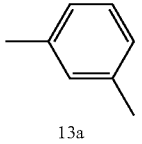
7a

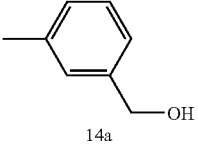
8a

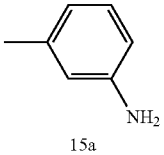
9a

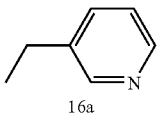
10a

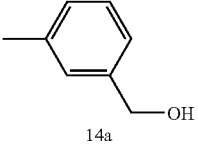
11a

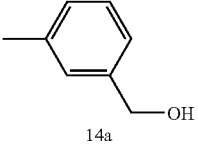
12a

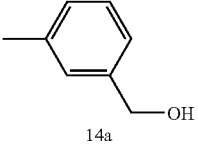
13a

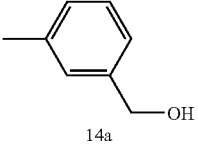
14a

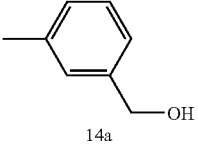
15a

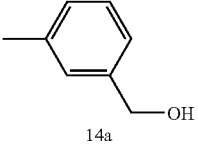
16a

TABLE 1-continued
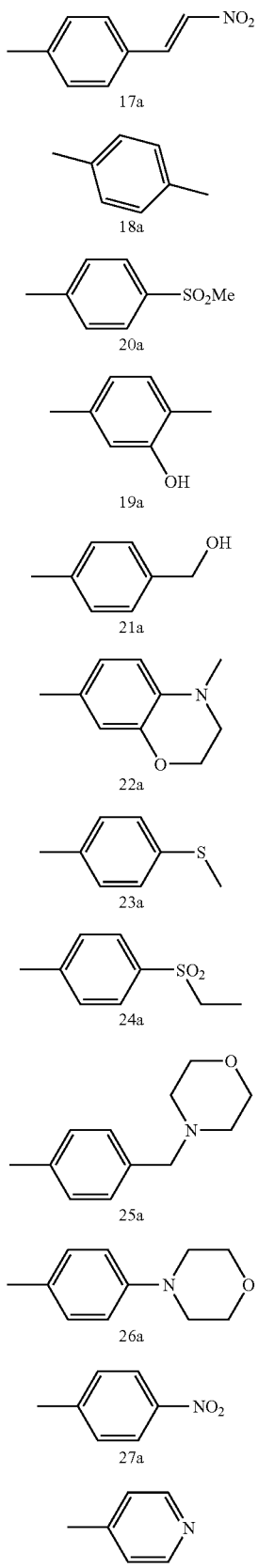
TABLE 1-continued
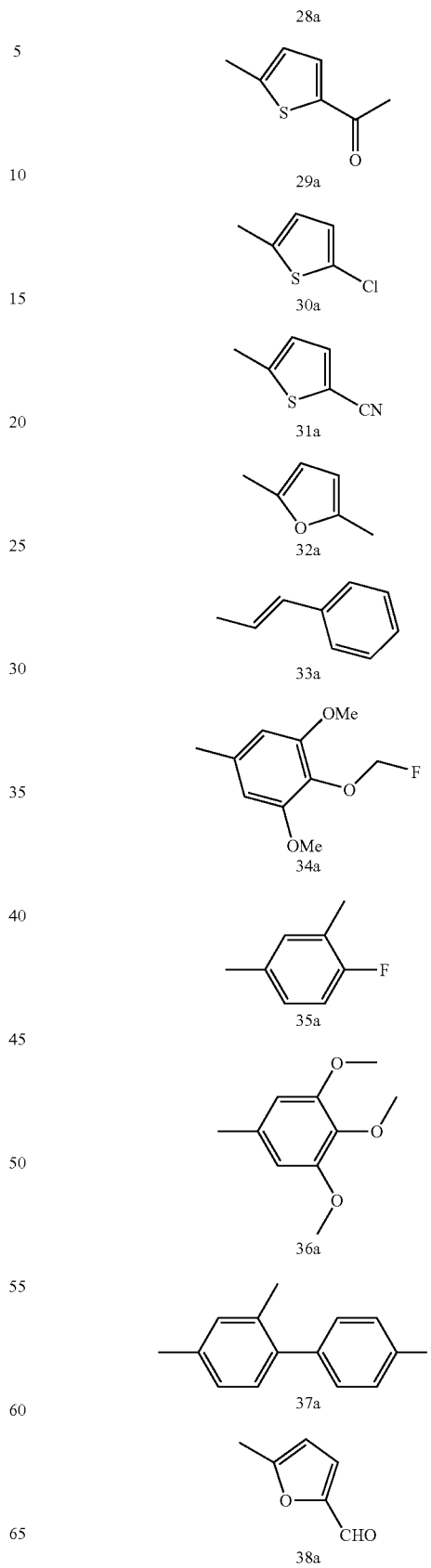

TABLE 1-continued
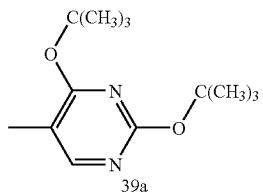
39a
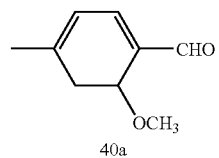
40a
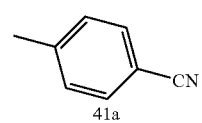
41a
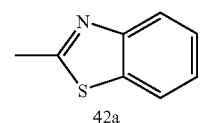
42a
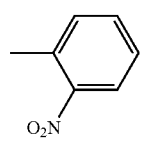
43a
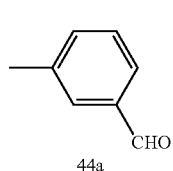
44a
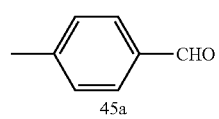
45a
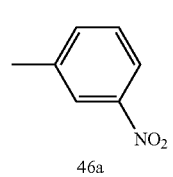
46a
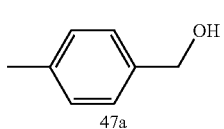
47a
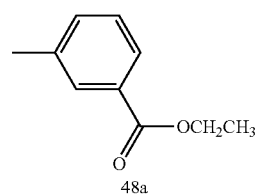
48a
TABLE 1-continued
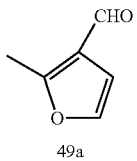
49a
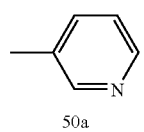
50a
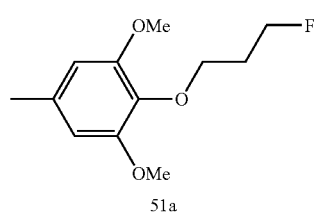
51a
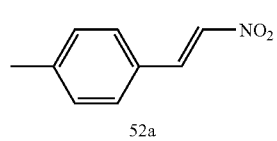
52a
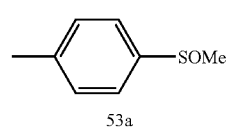
53a
In yet another embodiment, useful imaging agents include benzofuran derivatives such as those of the following Formula II:
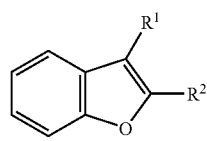
II
wherein $R^1$ and $R^2$ are as described above. More particularly, certain benzofuran derivatives having a formula as described in Table 2 are useful as imaging agents for A-beta.
TABLE 2
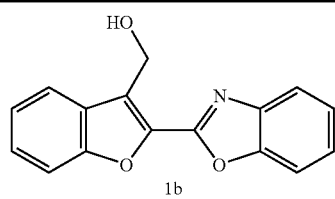
1b TABLE 2-continued
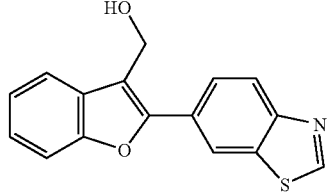
2b
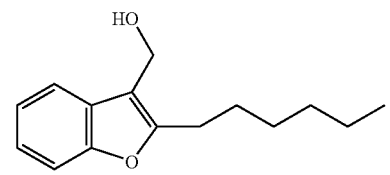
3b
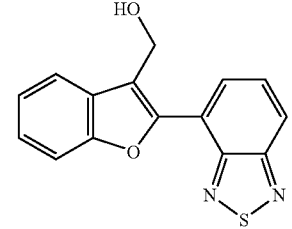
4b
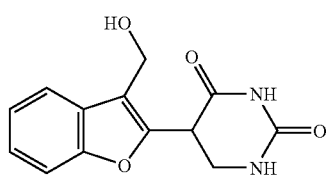
5b
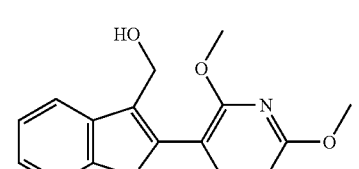
6b
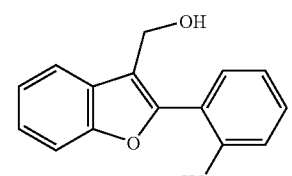
7b
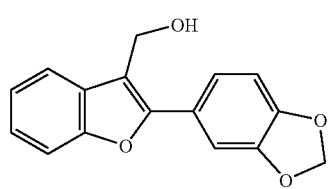
8b
TABLE 2-continued
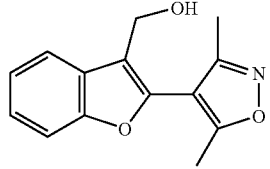
9b
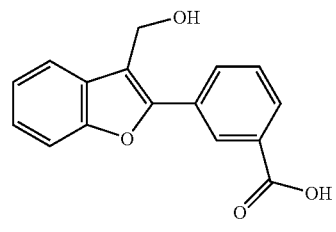
10b
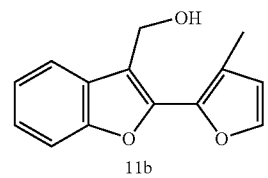
11b
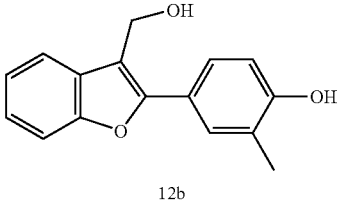
12b
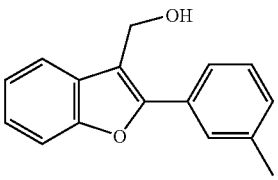
13b
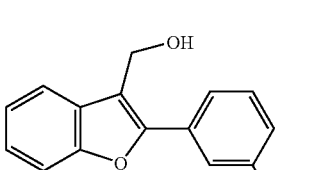
14b
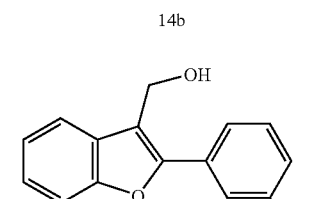
15b TABLE 2-continued
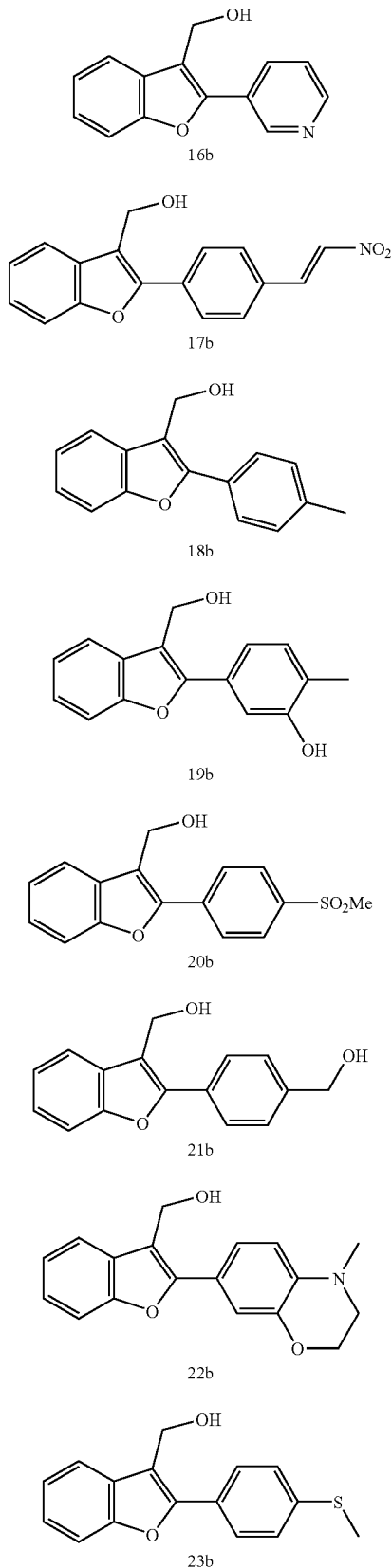
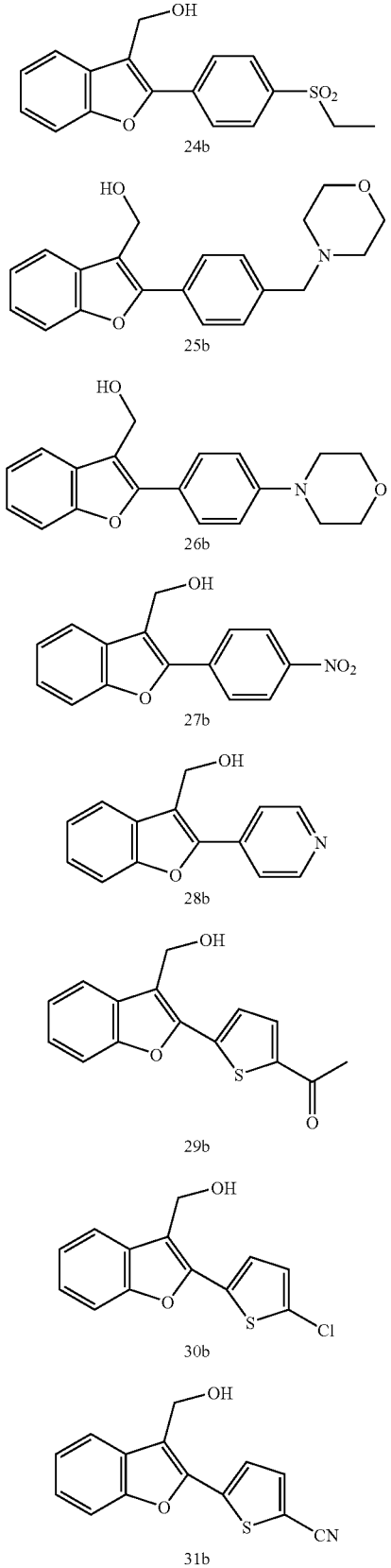

TABLE 2-continued
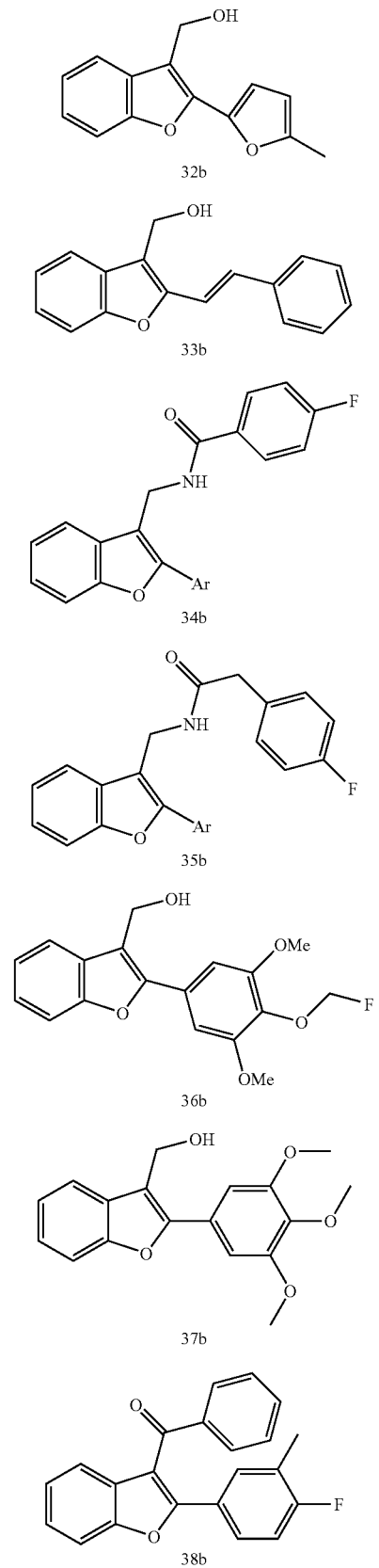
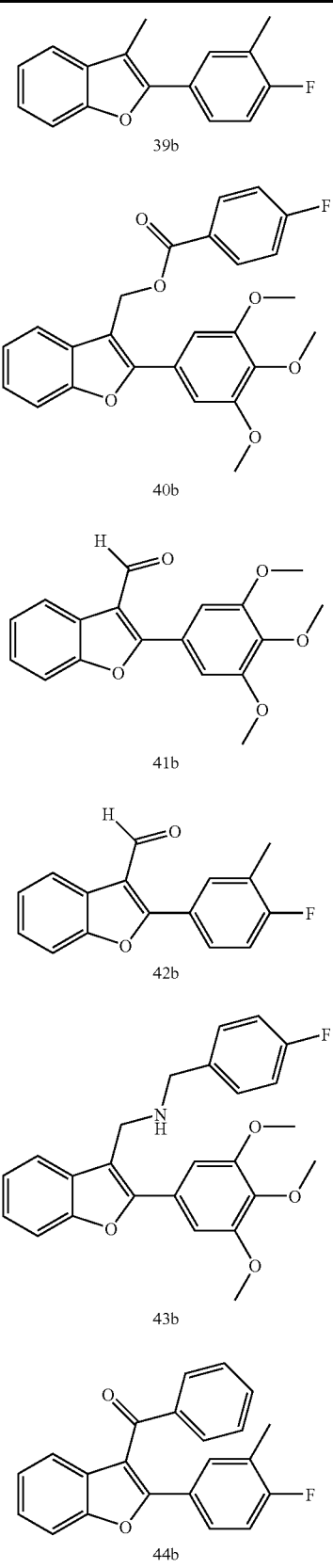

TABLE 2-continued
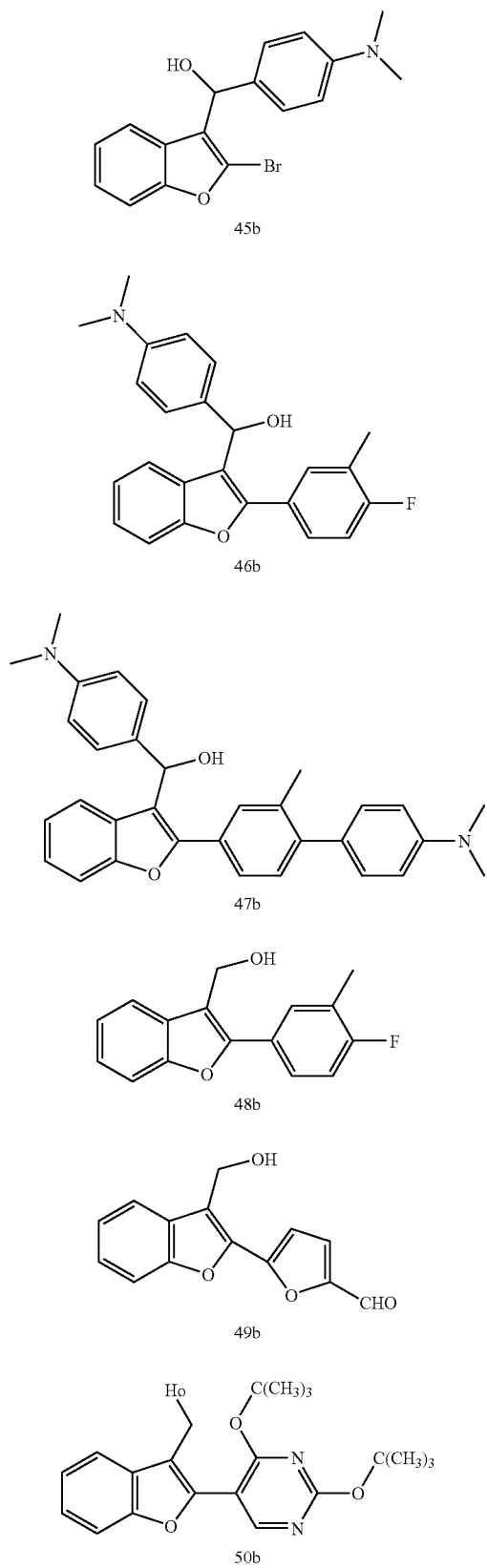
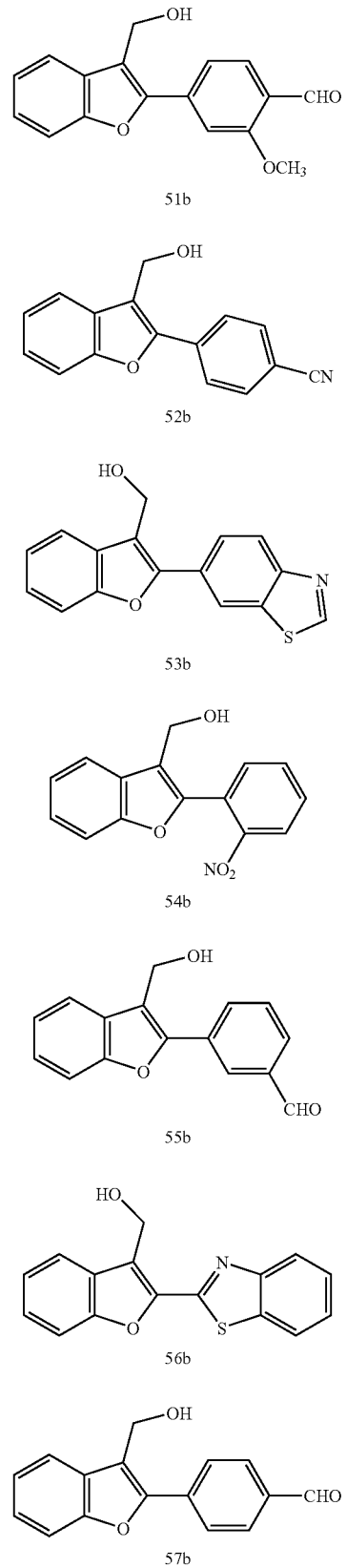

TABLE 2-continued

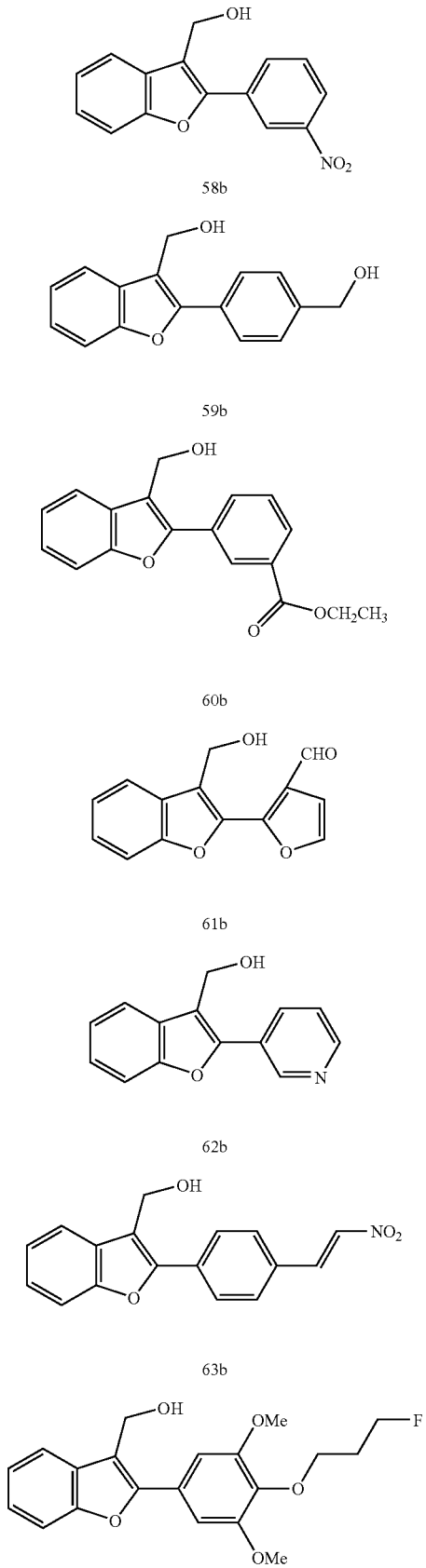

58b, 59b, 60b, 61b, 62b, 63b

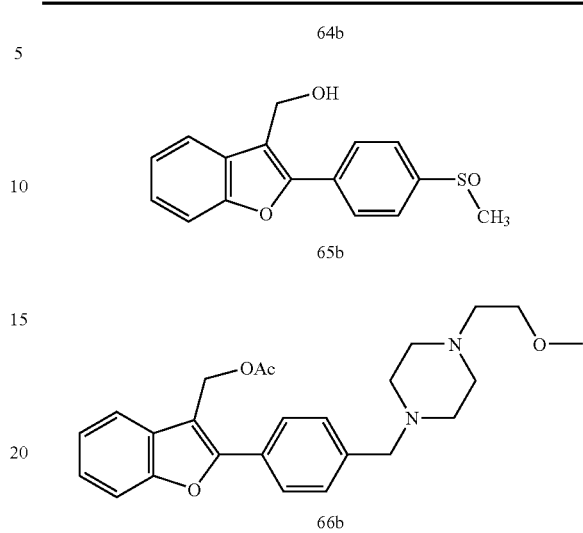

64b, 65b, 66b wherein Z is NH, O, S; Ar is substituted phenyl, pyridinyl, thiophenyl, furanyl, as in the examples above. As is known in the art, "Et" is ethyl and "Me" is methyl.

Substituted 2-phenyl-3-alkyl benzofurans similar to those shown in Formula II have been synthesized by the Lewis acid—mediated condensation of benzyl with phenols and aryl ethers, Palladium—catalyzed cross-coupling of benzyl ketones and α,β-unsaturated carbonyl and phenolic compounds with o-dibromobenzenes, and McMurry-type reductive cyclization of dicarbonyl compounds catalyzed by low-valent Ti. Also, 2,3-diphenyl benzofurans have been prepared by the cyclodehydration of α-aryloxydeoxybenzoins catalyzed by phosphoric acid. 2-Aryl-3-allylbenzofurans have been synthesized by the Pd-catalyzed cyclization of 2-alkynylphenols with allyl carbonates. Pd-catalyzed cyclizations are also the preferred method for the synthesis of a variety of 2-alkylbenzofurans and 2-arylbenzofurans.

In yet another embodiment, useful imaging agents include benzofuran derivatives such as those of the following Formula III:

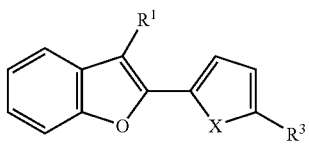

wherein $R^1$ is as described above, and R3 is an aryl, alkyl substituted aryl, particularly fluoroethyl substituted alkyl, substituted heteroaryl moieties such as furans, thiophenes, indoles, imidazoles, oxazoles, thiazoles, oxadiazoles, thiadiazoles and triazoles.

More particularly, certain benzofuran derivatives having a formula as described in Table 3 are useful as imaging agents for A-beta.

TABLE 3
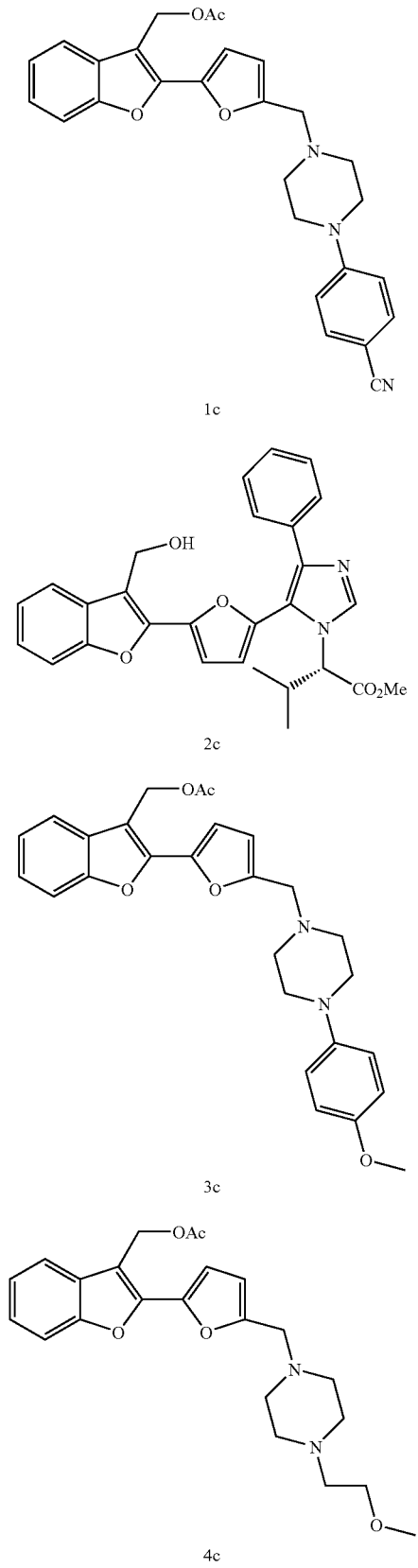
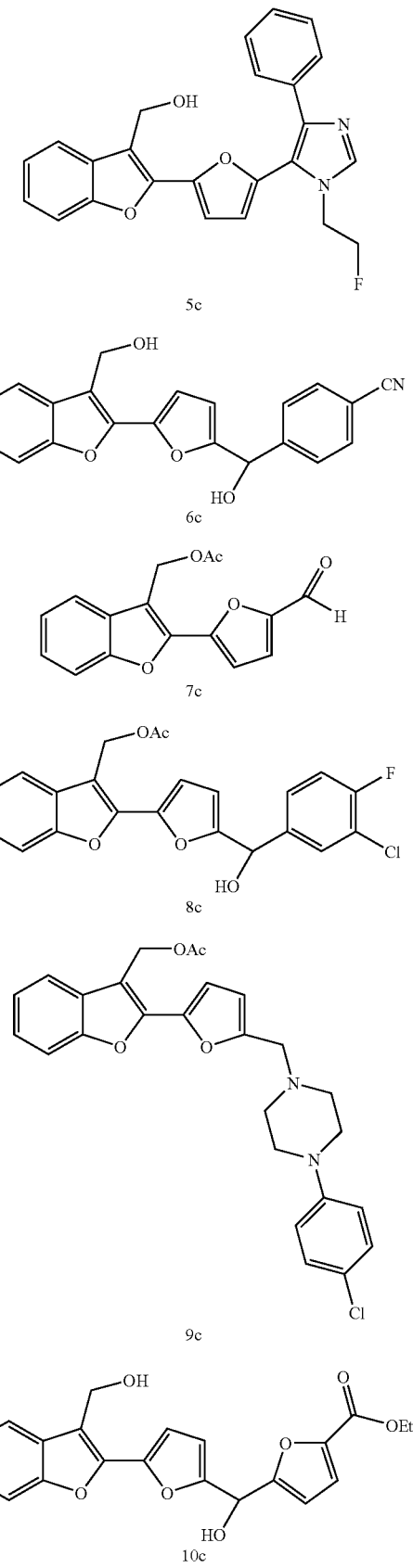

TABLE 3-continued

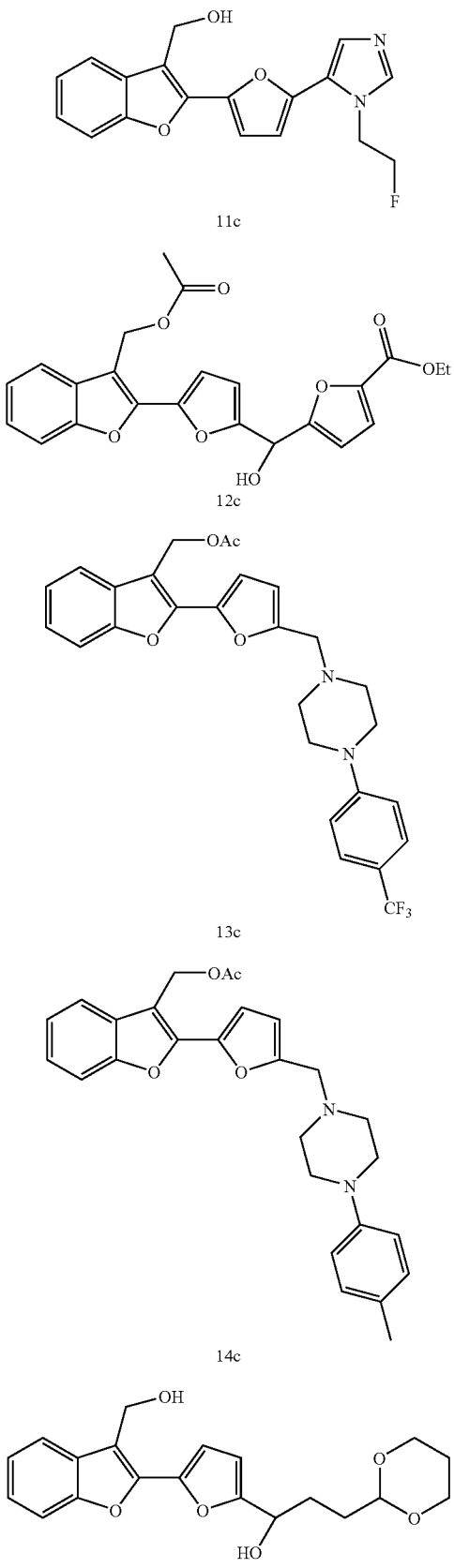

11c

12c

13c

14c

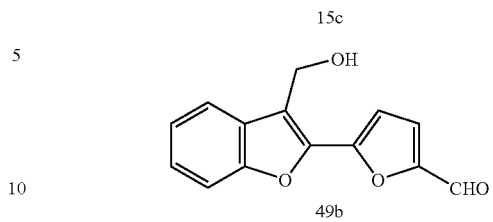

49b

Antibodies Against Soluble A-beta

Anti-A-Beta antibodies may be prepared against a suitable antigen or hapten comprising the desired target epitope, such as the junction region of the 1-42 A-beta oligomer consisting of amino acid residues 13-26. An alternative antigen or hapten may include the carboxy terminus consisting essentially of amino acid residues 33-42 of A-beta. One suitable antibody to soluble A-beta is disclosed in Kayed, et al., Science, Vol. 300, p. 486, Apr. 18, 2003 (incorporated by reference herein). The target haptens (e.g., synthetic peptides comprising an A-beta epitope) may also be prepared by conventional solid phase techniques, coupled to a suitable immunogen, and used to prepare antisera or monoclonal antibodies. Suitable peptide haptens typically will typically comprise at least five contiguous residues within A-beta and may include more than six residues. Synthetic polypeptide haptens may be produced by the Merrifield solid-phase synthesis technique in which amino acids are sequentially added to a growing chain (Merrifield (1963) J. Am. Chem. Soc. 85:2149-2156). Suitable antibodies may include, for example, those of antibodies described in U.S. Pat. Nos. 5,811,310; 5,750,349; and 5,231,000, R1282, 21F12, 3D6, FCA3542, and other monoclonal and polyclonal antibodies for A-beta 1-40, and/or A-beta 1-42 that demonstrate the ability to preferentially or specifically bind to soluble A-beta.

Activatable Agents

Imaging agents have been developed that may report on the specific presence of a target molecule without binding to that molecule. In such instances the imaging agents are considered "activatable" because their signal is activated or unactivated based on the presence of a specific target molecule. Examples of such agents have been used for MRI and optical imaging.

Signal Generators

In some embodiments, the soluble A-beta binding agent includes an intrinsic signal generator (e.g., a radiolabel or a fluorescent moiety) and requires no additional components to be observed using a selected modality (e.g., optical detection or radiography). In embodiments where the soluble A-beta binding agent does not include an intrinsic signal generator, the imaging agent may be supplemented with one or more signal generators capable of being detected by a particular imaging modality.

Examples of signal generators include, but are not limited to, fluorophores (e.g., cyanine dyes), radioisotopes, and paramagnetic ions. Suitable radioisotopes may include $^{3}H$, $^{11}C$, $^{14}C$, $^{18}F$, $^{32}P$, $^{35}S$, $^{123}I$, $^{125}I$, $^{131}I$, $^{51}Cr$, $^{36}Cl$, $^{57}Co$, $^{59}Fe$, $^{75}Se$, and $^{152}Eu$. Isotopes of halogens (such as chlorine, fluorine, bromine and iodine), and metals including technetium, yttrium, rhenium, and indium are also useful labels. Typical examples of metallic ions that may be used as signal generators include $^{99m}Tc$, $^{123}I$, $^{111}In$, $^{131}I$, $^{97}Ru$, $^{67}Cu$, $^{67}Ga$, $^{125}I$, $^{68}Ga$, $^{72}As$, $^{89}Zr$, and $^{201}Tl$.

For use with the present disclosure, radiolabels may be prepared using standard radiolabeling procedures well known to those skilled in the art. For example, the labeling will be accomplished by incorporation of one of the above-listed labels into one or both of the $R^1$ or $R^2$ groups into the benzofuran derivative shown as Formula I, Formula II, or Formula III.

The disclosed compounds may be radiolabeled either directly by incorporating the radiolabel directly into the compounds or indirectly by incorporating the radiolabel into the compounds through a chelating agent, where the chelating agent has been incorporated into the compounds. Such radiolabeling should also be reasonably stable, both chemically and metabolically, applying recognized standards in the art. Also, although the label may be incorporated in a variety of fashions with a variety of different radioisotopes, such radiolabeling should be carried out in a manner such that the high binding affinity and specificity of the unlabeled binding moiety is not significantly affected.

Preferred radioisotopes for in vivo diagnostic imaging by positron emission tomography ("PET") are $^{11}C$, $^{18}F$, 123I, and 125I, with $^{18}F$ being the most preferred. Typically, the labeled atom is introduced to the labeled compounds at a late stage of the synthesis. This allows for maximum radiochemical yields, and reduces the handling time of radioactive materials. When dealing with short half-life isotopes, an important consideration is the time required to conduct synthetic procedures, and purification methods. Protocols for the synthesis of radiolabeled compounds are described in Tubis and Wolf, Eds., "Radiopharmacy", Wiley-Interscience, New York (1976); Wolf, Christman, Fowler, Lambrecht, "Synthesis of Radiopharmaceuticals and Labeled Compounds Using Short-Lived Isotopes", in Radiopharmaceuticals and Labeled Compounds, Vol. 1, p. 345-381 (1973).

Paramagnetic labels may be metal ions are present in the form of metal complexes or metal oxide particles. Suitable paramagnetic isotopes may include $^{157}Gd$, $^{55}Mn$, $^{162}Dy$, $^{52}Cr$, and $^{56}Fe$. The paramagnetic label may be attached to the binding moiety by several approaches. One approach is direct attachment of one or more metal chelators to the binding moiety of the imaging agent. Alternatively, the binding portion of the imaging agent may be attached to a paramagnetic metal ion or heavy atom containing solid particle, or to an echogenic gas microbubble. A number of methods may be used to attach imaging agent, which specifically binds to soluble A-beta, to paramagnetic metal ion, or heavy atom containing solid particles by one of skill in the art of the surface modification of solid particles. In general, the imaging agent is attached to a coupling group that reacts with a constituent of the surface of the solid particle. The coupling groups may be any of a number of silanes, and also include polyphosphonates, polycarboxylates, polyphosphates or mixtures thereof, which react with surface hydroxyl groups on the solid particle surface, as described, for example, in U.S. patent application publication 2002/0159947 and which may couple with the surface of the solid particles, as described in U.S. Pat. No. 5,520,904.

The imaging agent itself may be fluorescent or may be tagged with a signal generator (e.g., an optical label that are fluorophores) such as fluorescein, rhodamine, Texas Red, and derivatives thereof. The optical label may be chemiluminescent, such as green fluorescent protein, luciferin, dioxetaneor. The soluble-A-beta binder may be linked to the portion of the signal generator using techniques known to those skilled in the art.

Binding Assays

Also provided herein are various methods for determining the ability of a putative binder to bind an A-beta species comprising the steps of: (a) applying one of the inventive compounds that bind soluble A-beta to a sample with at least one A-beta species; (b) applying a putative binder bind soluble A-beta to a the same or a separate sample; and (c) determining whether the putative binder binds to the A-beta species.

In some embodiments, the disclosed methods provide additional control steps wherein each of steps (a)-(c) are repeated using a one of the inventive compounds (i.e., a validated compound) in place of the putative binder to provide a positive control. Thus, for the positive control variant, steps (a)-(c) may be repeated using a validated binder in place of the putative binder. Likewise, for the negative control variant, steps (a)-(c) may be repeated using a validated non-binder in place of the putative binder. For either positive control or negative control variations the additional control steps (a)-(c) may be performed either in parallel or in tandem with the assay for the putative binder. In all embodiments including one or more control the methods may include the additional step of determining the relative binding of the putative binder and the validated binder or the validated non-binder. The determining binding step may entail any art recognized methods of determine binding in a tissue sample, for example optically observing the binding using fluorescence microscopy or radiographic imaging. Where the binder has an inherent ability to general a measurable signal when present in a sample (e.g. fluoresces or generates a radioactive signal), no additional agents are required for the determining binding step. If, however, the binder does not have the ability to generate signal, the disclosed methods additional steps of applying a signal generator to facilitate the binding determination step. Such an additional step may employ, for example, a labeled antibody that recognizes the binder.

Modes of Administration

The labeled imaging agent may typically be administered to a patient in a composition comprising a pharmaceutical carrier. A pharmaceutical carrier may be any compatible, non-toxic substance suitable for delivery of the labeled or unlabeled A-beta binding agents to the patient, including sterile water, alcohol, fats, waxes, proteins, and inert solids may be included in the carrier. Pharmaceutically acceptable adjuvants (e.g., buffering agents, dispersing agent) may also be incorporated into the pharmaceutical composition. Carriers may contain a solution of the imaging agent or a cocktail thereof dissolved in an acceptable carrier, preferably an aqueous carrier. A variety of aqueous sterile carriers may be used, e.g., water, buffered water, 0.4% saline, 0.3% glycine, or 25% human serum albumin.

The solutions or compositions comprising the soluble A-beta binding agents are preferably pyrogen-free, sterile, and generally free of particulate matter. The solutions or compositions may contain additional pharmaceutically acceptable substances as necessary to approximate physiological conditions such as pH adjusting and buffering agents, toxicity adjusting agents, for example sodium acetate, sodium chloride, potassium chloride, calcium chloride, sodium lactate.

The concentration of imaging agent in the composition or solutions may vary as required. Typically, the concentration will be in trace amounts to as much as 5% by body weight of the subject but with vary according to the particular imaging modality used. Typically, agent concentrations are selected primarily based on fluid volumes, and viscosities in accordance with the particular mode of administration selected. Preferably, the agent concentration is between about 0.1 and about 1 nmol, more preferably from about 0.1 nmol to about 0.5 nmol. The imaging agent may be present in several ml of injectable solution, as would be determined based on dose, and easily calculated by one of ordinary skill in the art. For example, if the agent is labeled with $^{18}F$, approximately 105 pmol of $^{18}F$ yields 10 mCi of a radiation dose initially. This amount of radioactivity is typical and considered safe in the current medical imaging procedures. A typical composition for intravenous infusion may be made to contain 250 ml of sterile Ringer's solution and up to 100 mg, preferably around 10 mg, of the soluble A-beta imaging agent. The composition containing the imaging agent may be combined with a pharmaceutical composition and may be administered subcutaneously, intramuscularly, or intravenously to patients suffering from, or at risk of, amyloid-related conditions such as AD.

In some embodiments, clearance time can be employed to permit the portions of the imaging agent to travel throughout the subject's body and bind to any available soluble A-beta while also permitting the unbound imaging agent to be cleared from the body or from the brain to thereby decrease noise resulting from non-bound imaging agent. In cases where the imaging agent does not directly bind, but rather reports on the presence of the A-beta, sufficient time is allowed for a specific interaction to occur in which the reporter molecule is activated. The clearance time will vary depending on the label chosen for use and may range from 1 minute to 24 hours.

The imaging agent may be delivered and the imaging taken to determine the amount of soluble A-beta present in the subject's body as an indication of disease or pre-disease states. The levels of soluble A-beta may be indicative of pre-disease conditions and therapies toward removal of the soluble A-beta or its precursors may prevent or forestall the onset of an amyloid-related disease, such as AD.

Therapeutic Efficacy

In another aspect, the present methods may be used to determine the efficacy of therapies used in a subject. By using multiple images over time, the levels of A-beta may be tracked for changes in amount and location. This method may aid physicians in determining the amount and frequency of therapy needed by an individual subject. In this embodiment, an imaging agent in accordance with the present disclosure is administered and a baseline image is obtained. The therapy to be evaluated is administered to the subject either before or after a baseline images are obtained. After a pre-determined period of time, a second administration of an imaging agent in accordance with their disclosure is given. A second or more images are obtained. By qualitatively and quantitatively comparing the baseline and the second image, the effectiveness of the therapy being evaluated may be determined based on a decrease or increase of the signal intensity of the second image or additional images.

EXAMPLES

The following non-limiting Examples are shown and describe various embodiments of the present invention.

Example 1

A-beta Species Formation

A. 1 mg of human beta-amyloid 1-42 (H-5642, Bachem) and 500 uL of 1,1,1,3,3,3 hexafluoro-2-propanol (HFIP) (Aldrich) were chilled in separate bottles on ice for 30 mins. Cold beta-amyloid 1-42 was solubilized with cold HFIP. The mixture was incubated for 1 hr at room temperature until it turned clear. The resulting solution was then dried to a film under vacuum. The film was dissolved again in cold HFIP and incubated another 1 hr at room temperature. The resulting solution was separated into aliquots in several microcentrifuge tubes. HFIP was removed under vacuum, and the films were stored at −20° C. until use. To prepare soluble oligomer, the film was dissolved in appropriate amount of dry DMSO (Sigma), and Ham's F12 media (Biosource) or PBS (Sigma, D8537) was added and incubated at 4° C. for 24 hours (final concentration of 200 uM or 0.9 mg/mL beta-amyloid in 2% DMSO). The tube containing the soluble oligomers was centrifuged at 13,000 rpm for 5 mins, and its supernatant was transferred to a clean tube.

B. Insoluble A-beta (1-40) fibril formation: Lyophilized human beta-amyloid 1-40 peptide (Catalog number H-1194, Bachem) was solubilized with HFIP to produce a dry clear film following the process described above for beta-amyloid 1-42. The clear film of beta-amyloid 1-40 was diluted with distilled water to achieve a 6 mg/mL concentration. If the resulting solution had a cloudy appearance, it was placed in an ultrasonic bath until the solution became clear. The clear solution was diluted to 1 mg/mL with PBS, pH 7.4 to obtain a final concentration of 1 mg/mL beta-amyloid 1-40, and then incubated at 37° C. on an orbital shaker at 200 RPM for 4 days. A cloudy solution was produced, and the fibril production was confirmed by measuring changes in fluorescence of Thioflavin T, as well as by atomic force microscopy and transmission electron microscopy. Fibrils were used immediately after their production was confirmed.

Example 2

Benzofuran Derivative Preparation

A. Preparation of 2-bromo-3-bromomethyl benzofuran: 2-bromo-3-bromomethyl benzofuran was prepared as described previously, using a modified procedure (*Helv. Chim. Acta* 1947, 30, 297). To a solution of 3-methylbenzofuran (4 g, 30.26 mmol) in carbon tetrachloride (20 ml) was added benzoyl peroxide (100 mg) and recrystallized N-bromosuccinimide (NBS) (10.8 g, 2 equivalents). The mixture was refluxed for 3 hrs. The product formation was followed by GC-MS. Following analysis, 1.1 g NBS was added and the mixture was refluxed for 1 hr. At this point, one more addition of NBS (1 g) followed by 1 hr of reflux proved necessary. The solvent was stripped and replaced with ethanol (1 2 ml), the mixture was cooled to −20 C, yielding a mass of yellow crystals, which were filtered at −25 C The crystals of 2-bromo-3-bromomethyl benzofuran were washed with ethanol 912 ml) at −40 C, filtered and dried overnight (yield 7.672 g, 87%), better than 95% pure by GC-MS, which was immediately used in the next step. MS (m/e): 291, 290, 289 (M$^+$), 211, 209, 183,181, 146, 102, 75.

B. Preparation 2-bromo-3-hydroxymethyl benzofuran. 2-bromo-3-bromomethyl benzofuran from Step A (7.672 g, 26.45 mmol) was dissolved in dioxane (30 ml), followed by a solution of NaHCO3 (2.67 g, 1.2 eq.) in water (30 ml). The mixture was refluxed for 1 hour while stirring vigorously, cooled to room temperature, diluted with water (150 ml) and extracted with dichloromethane (5×). The extract was washed with brine, dried over sodium sulfate, and the solvent was removed under reduced pressure. The resulting orange oil was dissolved in chloroform 912 ml and left to stand at −20 C. The resulting yellow prisms were filtered at −40C, washed with chloroform and filtered cold. Yield: 3.72 g (62%). MS (m/e): 228, 226 (M+), 211, 209, 183, 181, 171, 169, 147, 118, 102, 91. $^1$H-NMR (acetone-D$_6$): 4.29 (t,1H, J=6 Hz) 4.73 (d, 2H, J=6 Hz) 7.32 (m, 2H) 7.51 (d,1H,J=8 Hz) 7.78 (dd, 1H, J=8 Hz, 2 Hz). $^{13}$C-NMR (acetone-D$_6$): 54.74, 110.64, 119.96, 123.28, 124.57, 126.51, 128.12, 155.37.

C. Synthesis of 49b [2-(2-formyl-5-furanyl)-3-hydroxymethyl benzofuran]. To the microwave vial was added the bromo-benzofuran derivative from B (0.1 mmol), the 2-formylfuran-5-boronic acid (Aldrich) (1.5 eq.), potassium carbonate (1.5 eq.), palladium dibenzylidene acetone (0.03 eq.) and degassed dimethylacetamide (1 ml). The mixture was blanketed with N$_2$ and heated in the microwave at 120 C for 10 minutes (initial power 50 W). Water (2 ml) was added and the mixture was extracted with ether (4×) and the crude extract was adsorbed on silica gel and purified by MPLC (hexanes/ethyl acetate gradient).MS (m/e): 242 (M+), 225, 213, 196, 185, 168, 157, 139, 128, 102, 77. $^1$H-NMR (acetone-D$_6$): 5.15 (s, 2H), 7.19 (d, 1H, J=4 Hz), 7.35 (dd, 1H, J=8 Hz, 1 Hz), 7.44 (dd, 1H, J=8 Hz, 1 Hz), 7.56-7.65 (m, 2H), 7.93 (d, 1H, J=8 Hz), 9.76 (s,1H). $^{13}$C-NMR (acetone-D$_6$).

D. Preparation of 2-bromo-3-formyl benzo[b]furan. To a 50 ml round bottom flask were added powdered pyridinium chlorochromate (443 mg, 2.055 mmol), Celite® (450 mg) and dry dichloromethane (20 ml). A solution of the alcohol as in Formula I, wherein R$^1$=CH$_2$OH, R$^2$=Br, X=O (226 mg, 1 mmol) in dichloromethane (1 ml) was added and the mixture was stirred at r.t. in the dark for one hour. TLC (hexanes/ethyl acetate 4/1 v/v) indicated complete conversion (R$_f$ 0.7 vs. R$_f$ 0.3 for starting material). The mixture was diluted with ether, flushed through a 1 in plug of silicagel, the solvent was stripped and the residue was again flushed through a 1 in plug of silicagel, using hexanes/ethyl acetate 2/1 v/v. to give the desired product as light orange crystals (205 mg, 91%).

E. General procedure for the addition of organometallic reagents to aldehyde, as in Formula I, R$^1$=CHO, R$^2$=Br, X=O: To a dry 5 ml flask was added the aldehyde (0.2-1 mmol), dry ether (1.5 ml) and the mixture was cooled to 0 C. The organometallic reagent solution (1.25 equivalents) was then added dropwise and the mixture was stirred at 0° C. for 30 minutes. Then, GC-MS generally indicated complete conversion. The ether layer was washed with aqueous citric acid, dried and the compound was purified by MPLC using hexanes/ethylacetate gradient. When the corresponding ketone was the desired product, the crude secondary alcohol was oxidized according to the procedure outlined above.

F. General procedure for the reductive amination of 2-aryl-3-formyl benzofurans: To a 1 ml vial was added the aldehyde (0.05-0.1 mmol), dichloroethane (0.4 ml), 2 equivalents of the primary or secondary amine, 1 equivalent of AcOH and 1.5 equivalents of NaBH(Oac)3. The mixture was stirred vigorously at room temperature. Most reactions were complete in 4-10 hrs as evidenced by GC-MS analysis. The solvent was stripped with a nitrogen stream, ethyl acetate and silicagel (100-200 mg) was added and the crude product was purified by MPLC using the solid sample technique.

G. General procedure for the preparation of 2-aryl-3-aminomethyl benzofurans: i) To a dry vial was added triphenylphosphine (275 mg, 1.05 eq.) and phthalimide (149 mg, 1.02 eq.). The vial was stoppered and purged with N2. Dry THF (2 ml) was added followed by a solution of the alcohol 2 (as in Formula I, R$^1$=CH$_2$OH, R$^2$=Br, X=O) in THF (1 ml) and immediately by diisopropyl-azo-dicarboxylate (DIAD), dropwise. The mixture warmed up as the phthalimide dissolved, and the vial was cooled with an air stream. The resulting yellow solution was stirred at r.t. for 14 hrs. Silicagel was added to the reaction mixture and the solvent was stripped. The desired 2-bromo-3-(phthalimidomethyl)benzofuran was obtained in 84% yield following purification by MPLC using hexanes ethyl acetate 0-40% v/v gradient; ii) Introduction of various aryl moieties at the 2 position, using the intermediate above, proceeded smoothly following the general Suzuki coupling methodology described above; iii) Deprotection of the 2-aryl-3-benzofuranylmethyl phthalimides thus obtained was achieved following treatment of the corresponding intermediate, as a 0.1M solution in isopropanol, with 1.05 equivalents of N,N-dimethyl-1,3-propane diamine and microwave irradiation at 110 C for 10 minutes. Upon addition of silicagel the solvent was stripped off and the desired amine was obtained following MPLC using hexanes/ethyl acetate containing 0.1% triethylamine.

Intermediates 34b, 35b (amides, ureas, urethanes in the compounds table) were prepared as follows: to a dry vial containing the amines (example NN1, c) (0.1 mmol in 1 ml dry dichloromethane) was added the isocyanate 1.05 eq. and the mixture was stirred at room temperature for 4 hrs or until GC-MS analysis indicated complete conversion. The solvent was stripped, the residue taken in 1 ml ethyl acetate and filtered through a 3 ml SPE cartridge (silicagel) using ethyl acetate. The product was >95% pure (GC-MS) and was used without further purification. Similarly, acid chlorides were used for the synthesis of amides; in this case, 1 eq. of triethylamine was used as an acid quencher. This procedure was also used for the synthesis of urethanes, when 1.25 eq. of chloroformate was generally needed for the reaction to proceed to completion. Filtration through an SPE cartridge of basic alumina produced compounds of sufficient purity to be used without further MPLC purification.

Example 3

Radiolabeling of 49b

A. Preparation of [$^3$H]2-bromo-3-hydroxymethyl benzofuran. To aldehyde 2-bromo-3-formyl-benzofuran (15 mg, 66 µmol) in propan-2-ol:water 4:1 (600 µl) was added a solution of NaBT$_4$ (5 Ci @ approx. 56 Ci/mmol) in propan-2-ol:water 4:1 (600 µl). The solution was then stirred at room temperature for 2 hours. The residue was dissolved in ethyl acetate (5 ml) and a sample was analyzed by silica TLC eluting in dichloromethane:methanol (95:5). Yield: 15 Ci/mmol, 260 mCi (17 µmol).

B. Preparation of [$^3$H]2-Br-3-acetoxymethyl benzofuran. Three equivalents of acetic anhydride (5 µL) was added to 17 µmol of [$^3$H]2-bromo-3-hydroxymethyl benzofuran, and the acetylation was monitored by TLC. After 2 hours, an additional 10 µl of acetic anhydride was added and the mixture was swirled and left overnight. After a total of 18 hours the reaction proceeded approximately 50%. A further 50 µl of acetic anhydride was added and the mixture was left for a further 2 hours. An additional 50 µl of acetic anhydride was added and the reaction mixture was left for a second night, after which the reaction appeared to have progressed to near completion.

The crude mixture was purified by HPLC using an Ultrasphere (Beckman Coulter) ODS column eluting with a 0.1% TFA in water/acetonitrile gradient. The [$^3$H]2-Br-3-acetoxymethyl benzofuran fractions were rotary evaporated to dryness.

C. Preparation of [$^3$H]49b from [$^3$H]2-Br-3-acetoxymethyl benzofuran. To [$^3$H]2-Br-3-acetoxymethyl benzofuran (100 mCi) was added K$_2$CO$_3$ (1.4 mg), 5-formyl-furan-2-boronic acid (1.4 mg), Pd$_2$dba$_3$ (0.2 mg), and degassed dimethylacetamide (400 µl). The mixture was blanketed under nitrogen gas and heated with stirring at 80° C. for 6 hours. The reaction mixture was analyzed by TLC silica eluting in $CH_2Cl_2$:MeOH (95:5).

Deacetylation was performed by adding sodium hydroxide, 0.5 mg in THF:methanol (1:1), to the mixture. The reaction was swirled and stirred at room temperature. Samples were periodically analyzed by TLC and after 3 hours the reaction mixture was rotary evaporated to a lower volume and applied to a 2 g Sep-Pak cartridge. The required fraction was counted and analyzed and purified by HPLC using an Ultrasphere C18 column eluting with a water/methanol gradient, followed by another purification by HPLC using an Ultrasphere C18 column eluting with a water/acetonitrile gradient. The final product was analyzed by HPLC and mass spectrometry. Yield: specific activity of 13 Ci/mmol and 96.7% radiochemical purity.

Example 4

Binding Assays

The selectivity of 49b was demonstrated by two independent assays: an ex vivo fluorescent binding assay and scintillation proximity assays ("SPA"). The use of an ex vivo assay with naïve rat brains had the advantage of (1) decreasing confounding factors of target heterogeneity that exists in transgenic animals, and it demonstrated the potential usefulness of selectively binding probes such as 49b to (2) localize oligomers in the context of brain tissue.

Figure 1:
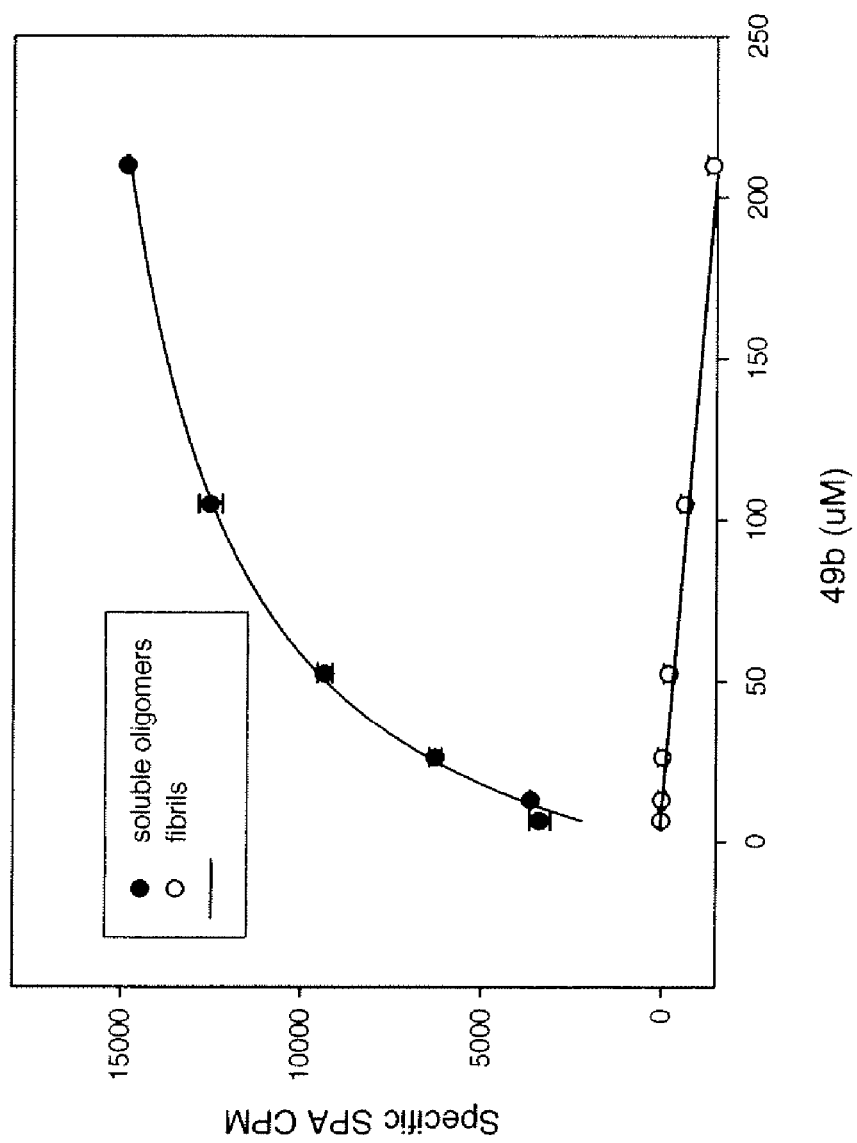
FIG. 1 depicts SPA saturation binding curve of $^3$H-49b with soluble A-beta oligomers and fibrils.

SPA employs direct binding of a radiolabeled probe, and demonstrated both saturability and self-competition. We calculated a Kd of 50 µM for soluble oligomers with no measurable affinity to fibrils (FIG. 1). Significantly, 49b shows no affinity against fibrils even at high concentration, suggesting greater selectivity than reported antibodies.

For SPA and atomic force microscopy (AFM) experiments, preparations of soluble oligomers and fibrils contained 20% biotinylated beta-amyloid 1-42 and 1-40, respectively (H-5642, H-5914, Bachem).

Example 5

Scintillation Proximity Assay

Lyophilized Streptavidin-Ysi beads (GE Healthcare) were reconstituted to 100 mg/mL in deionized water, and then further diluted in deionized water to give a suspension containing 0.25 mg/10 µl water. Unlabeled 49b and other benzofuran probes were dissolved in DMSO to give a final stock concentration of 15 mM.

For the saturation-binding assay, isotopic dilution of radiolabeled 49b with unlabeled 49b was performed. $^3$H-49b was added to 500 uM of unlabeled 49b to a final concentration of 50 µCi/mL $^3$H-49b. The probe solution was then serially diluted in PBS to give six solutions giving 6.6, 13.1, 26.3, 52.5, 105, or 210 uM in the final assay well. Each concentration of the probe solution was incubated with 12 µg beta-amyloid 1-42 oligomer (20% biotin) or 1-40 (20% biotin) fibrils in a total volume of 90 µl. Assays were incubated at room temp for 2 hrs before addition of 10 µL YSi-streptavidin (0.25 mg) SPA bead. Assays were set-up in triplicate in 96-well NBS plates (Costar). Assays were incubated overnight and counted the following morning. Tritium-labeled 49b was compared with tritium-labeled cimetide, caffeine, and AZT in binding to soluble oligomers (FIG. 3). The specific activities of the four probes were different, however the level of activity was the same at the concentrations where the probes were tested. For this assay, 130 nM of $^3$H-49b, 90 nM $^3$H-cimetidine, 14 nM $^3$H-caffeine, and 6 nM $^3$H-AZT were tested for direct binding to 12 ug of beta-amyloid-42 oligomer (20% biotin). Assay conditions were the same as described in saturation binding assay.

Tritium-labeled 49b was compared with two other tritium-labeled benzofuran derivatives in binding to soluble oligomers. The specific activities of $^3$H-49b, 37b, and 66b were similar to one another. For this assay, 130 nM of $^3$H-49b, $^3$H-66b, $^{and}$ $^3$H-37b were tested for direct binding to 12 ug of beta-amyloid-42 oligomer (20% biotin). Assay conditions were the same as described in saturation binding assay. Representative data is shown in FIG. 4.

Figure 2:
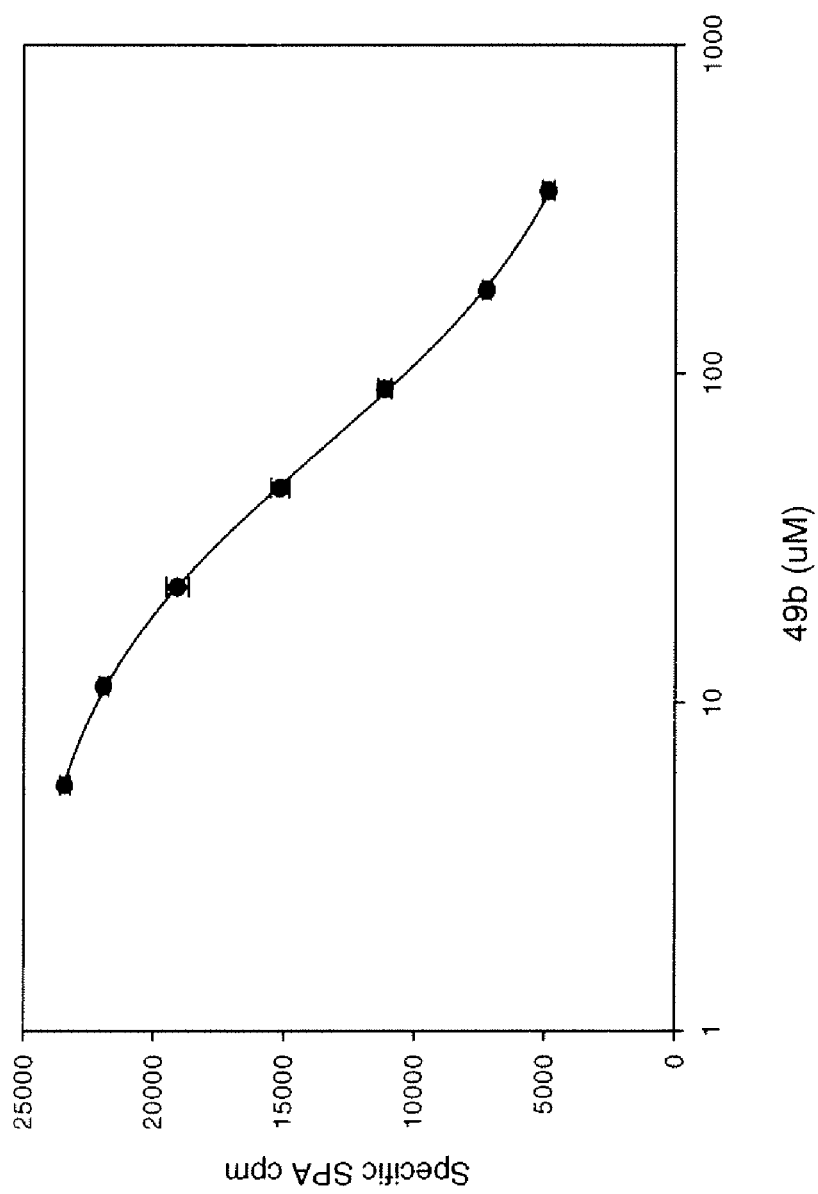
FIG. 2 shows SPA self-competition assay between labeled and unlabeled 49b on soluble A-beta oligomers.

For the self-competition binding assay, assay wells contained 130 nM $^3$H-49b and the indicated amount of unlabeled 49b (FIG. 2). Assay conditions were the same as described in saturation binding assay.

Data analyses were performed using Sigma Plot or GraphPad Prism® version 4. Curves were fitted using non-linear regression. $K_D$ values and $IC_{50}$ values were estimated from the binding curves.

For the competition binding assay between tritium-labeled 49b and various unlabeled benzofuran analogs, assays contained 130 nM $^3$H-49b and 50 uM of each of the unlabeled benzofuran analogs. As controls, 10 uM and 50 uM of unlabeled 49b were included in the assays. Representative data is shown in Table 4 below.

TABLE 4

| Compound | % Inhibition |
| --- | --- |
| No competitor control | 0 (no inhibition) |
| 49b (10 microMolar) | 29 |
| 49b (50 microMolar) | 61 |
| 1c | 24 |
| 2c | 30 |
| 3c | 38 |
| 4c | 41 |
| 5c | 48 |
| 6c | 51 |
| 7c | 51 |
| 8c | 51 |
| 9c | 55 |
| 10c | 57 |
| 11c | 58 |
| 12c | 59 |
| 13c | 60 |
| 14c | 60 |
| 15c | 68 |

A direct binding assay using tritium labeled 49b was performed against oligomers or fibrils by scintillation proximity assay (SPA). Beta-amyloid containing 20% biotin and tritiated 49b were incubated in solution for two hours prior to addition of the Ysi-Streptavidin beads. While the binding reaction was done in solution, we wished to determine if beta-amyloid soluble oligomers and fibrils retained their respective conformation when bound to the SPA beads by AFM.

In the AFM studies, PVT-streptavidin SPA beads were used in place of Ysi-streptavidin beads because the smoother surface of the PVT beads enhanced visibility of the bound beta-amyloid. AFM on PVT-streptavidin beads demonstrated that the soluble oligomers and fibrils maintained distinct structure when bound to beads (FIG. 5B, 5E).

Saturation binding of 49b indicated a $50 \times 10^{-6}$ mol/L binding constant when incubated with oligomers and a Bmax of 60-80 nmol/mg beta-amyloid, or a molar ratio of 1 probe: 3-4 beta-amyloid). No demonstrable affinity could be measured when 49b was incubated with immobilized fibrils under identical conditions (FIG. 1). Tritium labeled 49b binding to oligomers was competed by unlabeled 49b with an $IC_{50}$ of 60 µM (FIG. 2). Tritium labeled non-benzofuran compounds (AZT, cimetidine, caffeine) did not bind to soluble oligomers indicating specificity of the benzofuran class (FIG. 3). Further, a set of substituted benzofuran analogues (Table 4) showed a wide range of response in competing with binding of tritium labeled 49b.

Example 6

AFM Imaging of A-beta

Example 7

Ex vivo Assay Using Brains of Naïve Rats

Fresh-frozen tissue sections of Sprauge-Dawley naïve rat brain (Taconic) 10 microns in thickness were fixed with 10% formalin in PBS. Each section of the rat brain was then embedded in paraffin, an optional step that increases the shelf life of the sample.

Pre-formed soluble oligomers (100 µM), fibrils (100 µM), or monomers were applied onto tissues, and the slides incubated in a humidified chamber for two hours at 37° C. The slides were washed with PBS three times, then incubated with blocking buffer consisting of 10% normal goat serum in 3% BSA in PBS. To verify the presence of beta-amyloid, 100 µL of a $1/250^{th}$ dilution of anti-beta-amyloid antibody, 6E10 (Signet Laboratories) was applied onto the tissues. The slides were incubated for 1.5 hours at room temperature or for 45 mins at 37° C. 1 mM stock solutions of 49b and Thioflavin T were prepared in 50% ethanol. The probes were diluted to 50 µM in blocking buffer. 100 µL of each probe was added on to the slides containing 100 µL of 6E10. 6E10 antibody was not removed prior to addition of the probes. The slides were incubated in a humid chamber for 1 hour at room temperature then washed three times with PBS.

A $1/100^{th}$ dilution of the secondary antibody Alexa Fluor 594-goat anti-mouse IgG (Molecular Probes) in PBS was applied onto the slides, and incubated at room temperature for 1.5 hours. Slides were washed three times in PBS. Slides were coverslipped with AntiFade Gold (Molecular Probes) and incubated at least 4-6 hours before imaging. Microscopic examination and imaging was performed using a Leica wide-field fluorescence microscope using filter cube A (band pass 340-380 nm with a 400 nm dichroic mirror and a long pass 400 nm suppression filter) for 49b, cube E4 (band pass 436 nm with 455 dichroic mirror and a long pass 470 nm suppression filter) for Thioflavin T, and TX2 (band pass 520-600 nm with 595 nm dichroic mirror and 645/75 band pass suppression filter) for 6E10 immunostaining.

TABLE 5

| CUBE | Band Pass (nm) | Dichroic Mirror (nm) | Long Pass Suppression Filter (nm) | Band Pass Suppression Filter |
|---|---|---|---|---|
| Filter Cube A | 340-380 | 400 | 400 | NA |
| TX2 | 520-600 | 595 | NA | 645/75 |
| E4 | 436 | 455 | 470 | NA |

Example 8

Histochemical Staining on the PDAPP Transgenic Mouse 3-month old and 24-month old PDAPP mouse brains were obtained from Eli Lilly (Indianapolis, Ind.). Fresh frozen 30 micron sections of the brains were fixed in 10% formalin. For 49b, or Thioflavin S staining, 1 mM stock solutions of 49b and Thioflavin S were prepared in 50% ethanol. The probes were diluted to 25 µM in 50% ethanol, and then applied onto the PDAPP brain sections. The slides were incubated in a humid chamber at room temperature for 1 hr. The slides were washed three times with PBS and mounting medium (Molecular Probes) was added. The slides were incubated at least 4-6 hours before imaging. For the carbonate pre-treatment of the brain sections, formalin-fixed sections were incubated with 100 µL of carbonate buffer containing 0.025 M sodium chloride and 0.1 M sodium carbonate for 45 mins at 37° C. The slides were washed three times with PBS, then 49b or Thioflavin S were applied on the slides as described above. Microscopic examination and imaging was performed using a Leica wide-field fluorescence microscope using filter cube A for 49b and cube E4 for Thioflavin S. Co-staining of the probes with 6E10 anti-beta-amyloid antibody in the PDAPP brain sections was described in the ex vivo assay using naïve rats.

Example 9

Ex Vivo Assay

Beta-amyloid fibrils and oligomers were produced from synthetic peptide for binding assays and were demonstrated to have the expected distinct structural features as shown by AFM (FIG. 5A, 5D). A directed library of substituted benzofurans was synthesized based on a benzofuran series that was described above to prevent the formation of higher order fibrillar structuring of beta-amyloid. Most of the benzofurans synthesized exhibited inherent fluorescence, so we designed a unique ex vivo binding assay to test if the probes had the potential to differentiate soluble oligomers from fibrils by fluorescence microscopy. Fresh frozen rat brains from naïve animals were incubated with pre-formed oligomers or fibrils on separate sections. Anti-beta-amyloid antibody immunoreactivity and Thioflavin T staining confirmed the immobilization and localization of oligomers and fibrils (FIGS. 6A and C, top panel).

A preliminary screening using this ex vivo assay was performed. One of the probes that demonstrated robust differential binding between soluble oligomers and fibrils is the benzofuran 49b. This probe exhibited an excitation peak at 350-370 nm and an emission maximum at 470 nm. Incubation of 49b on these sections resulted in clear staining of oligomers with low background (FIG. 6B, bottom panel). Co-localization of beta-amyloid staining and 49b confirmed this probe interacted with beta-amyloid oligomers. No staining was observed when incubated on immobilized fibrils (FIG. 6D, bottom panel). 49b did not stain beta-amyloid 1-42 monomers or 1-40 monomers (data not shown).

Example 10

Binding in AD Animal Model

Brain sections from 24-month old PDAPP mice incubated with 49b demonstrated a punctuate staining pattern that co-localized with beta-amyloid immunoreactivity (FIGS. 7A and B). No staining was observed in young (3-month old) PDAPP mouse brains by either immunostaining by 6E10 or 49b (FIG. 7C), confirming that 49b specifically binds soluble beta-amyloid.

Significantly, 49b staining was primarily found in the hippocampus and co-localized with Thioflavin S staining in the 24-month old PDAPP brain sections (FIG. 8). Since 49b and Thioflavin S have similar spectral properties, co-localization was demonstrated by staining the sections first with 49b, washing the sections until the signal from 49b was not detectable, then staining with Thioflavin S. To confirm that 49b recognized oligomers, PDAPP brain sections were pre-treated with carbonate extraction buffer to remove soluble material. This buffer was previously used to remove pools of soluble beta-amyloid in the brain tissues without removing beta-amyloid plaques 49b did not stain carbonate pre-treated brain sections, although Thioflavin S staining remained (FIG. 9). Combined, these data support the conclusion that the in vivo selectivity of 49b and further indicates that beta-amyloid soluble oligomers colocalize with fibrillar beta-amyloid in the PDAPP transgenic mouse model.

Example 11

Fluorescence Titration Assays

Fresh solutions of 2-4 mM probe in methanol were appropriately diluted with PBS (pH 7.4) to obtain assay solutions with final concentration range of 0.1 nM to 100 μM probe in 300-400 μL PBS (pH 7.4, 2% methanol) with 10 μM A-beta (1-40) fibrils or 6.6 μM soluble A-beta (1-42). A duplicate series of assay solutions were aliquoted with the volume of soluble A-beta or fibrils replaced by PBS. The set of solutions with probe and soluble/fibrillar A-beta and the duplicate set without A-beta were prepared and the fluorescence spectra measured in triplicate. Spectral changes in the probe's fluorescence emission spectra that were unique to the presence of A-beta indicated specific binding interactions between the probe and A-beta species. This unique spectral change allowed for the determination of the probe's binding affinity. Fluorescence emission spectra for binding affinity determinations are measured with fluorometric instrumentation known to those skilled in the art, including at least a spectrofluorometer and spectrograph. Equilibrium dissociation constants were calculated using a one-site saturation model of binding.

Select benzofuran congeners exhibited nanomolar binding affinity to soluble A-beta (1-42) but no appreciable binding to A-beta (1-40) fibrils, as determined by fluorescence binding assays. A spectral change of a probe's fluorescence that is unique to the presence of soluble or fibrillar A-beta was used to calculate the binding affinity of a probe. For example, the 22 nM $K_D$ value (Table 6) indicates the selective binding of 37b (Table 2) for soluble A-beta beta with a characteristic increase in fluorescence intensity (and quantum yield) approaching approximately 5 times the fluorescence intensity (and quantum yield) of 37b in 2% methanol in PBS. 37b in 10 μM of A-beta (1-40) fibrils had minimal specific binding to the fibrils as demonstrated by an absence of significant enhanced fluorescence intensity in the presence of fibrils. 39b (Table 6) is an example of a benzofuran derivative that specifically binds to A-beta (1-40) fibrils instead of soluble A-beta 42 suing the SPA assay. In contrast, 38b neither binds to A-beta in soluble nor insoluble fibrillar form.

TABLE 6

| Compound | $K_D$ of compound to soluble A-beta (1-42) | $K_D$ of compound to insoluble A-beta (1-40) fibrils |
| --- | --- | --- |
| 38b | Nonspecific binding | Nonspecific binding |
| 39b | No binding <100 μM | 1.68 μM |
| 37b | 22.8 nM | No binding <100 μM |

While the invention has been illustrated and described in typical embodiments, it is not intended to be limited to the details shown, since various modifications and substitutions may be made without departing in any way from the spirit of the present invention. As such, further modifications and equivalents of the invention herein disclosed may occur to persons skilled in the art using no more than routine experimentation, and all such modifications and equivalents are believed to be within the spirit and scope of the invention as defined by the following claims.

We claim:

1. A compound of formula III

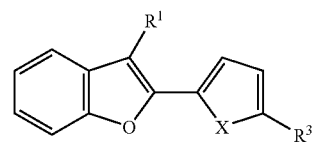

wherein X is oxygen, nitrogen, or sulfur;

$R^1$ is substituted or unsubstituted alkyl, hydroxy, amide, urea, or urethane; and $R^3$ is halogen, formyl, $C_1$-$C_{32}$ substituted or unsubstituted, branched or straight chain alkyl, cycloaliphatic, aryl, arylalkyl, or heteroaryl; and a label selected from radioisotopes, paramagnetic particles, and optical particles.

2. The compound of claim 1, wherein the label is a radioisotope selected from $^3$H, $^{11}$C, $^{14}$C, $^{18}$F, $^{32}$P, $^{35}$S, $^{123}$I, $^{125}$I, $^{131}$I, $^{51}$Cr, $^{36}$Cl, $^{57}$Co, $^{59}$Fe, $^{75}$Se, and $^{152}$Eu.

3. The compound of claim 2, wherein the wherein the label is a radioisotope selected from $^3$H, $^{11}$C, $^{14}$C, $^{18}$F, $^{32}$P, $^{35}$S, 123I, $^{125}$I, $^{131}$I, $^{36}$Cl, and $^{75}$Se.

4. The compound of claim 1, wherein the label is a paramagnetic particle selected from $^{157}$Gd, $^{55}$Mn, $^{162}$Dy, $^{52}$Cr, and $^{56}$Fe.

5. The compound of claim 1, wherein the label is an optical particle.

6. A compound according to claim 1, wherein R3 is selected from

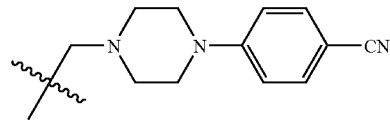

-continued
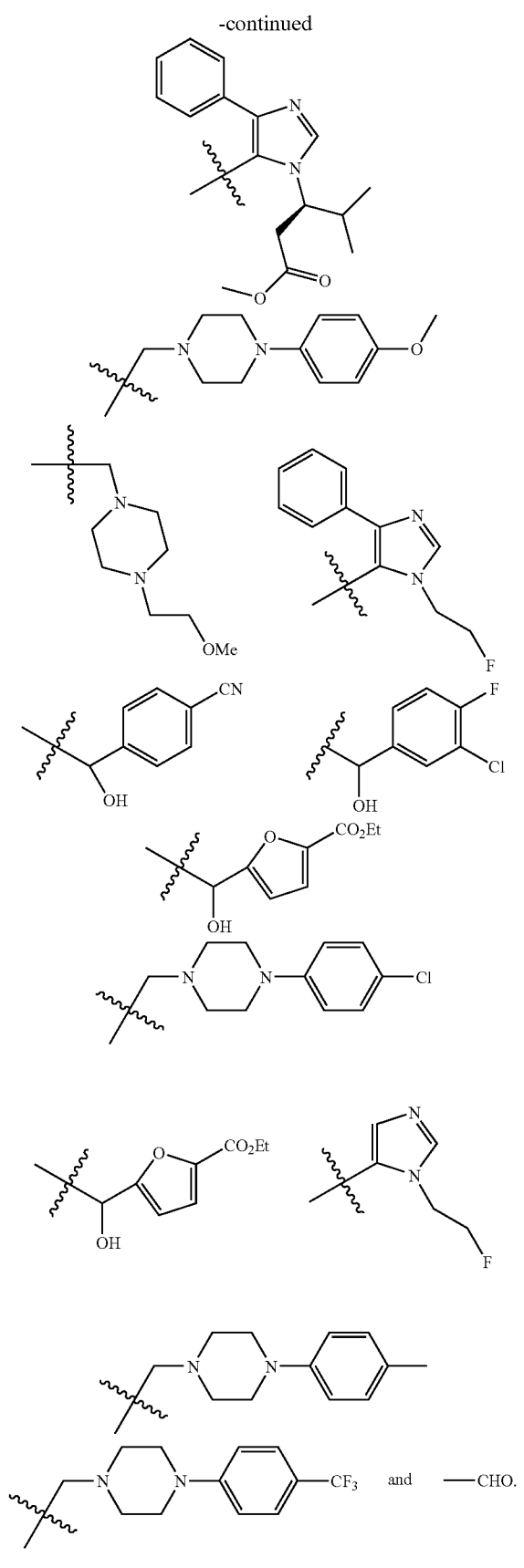
7. A compound according to claim 1, wherein formula III is selected from
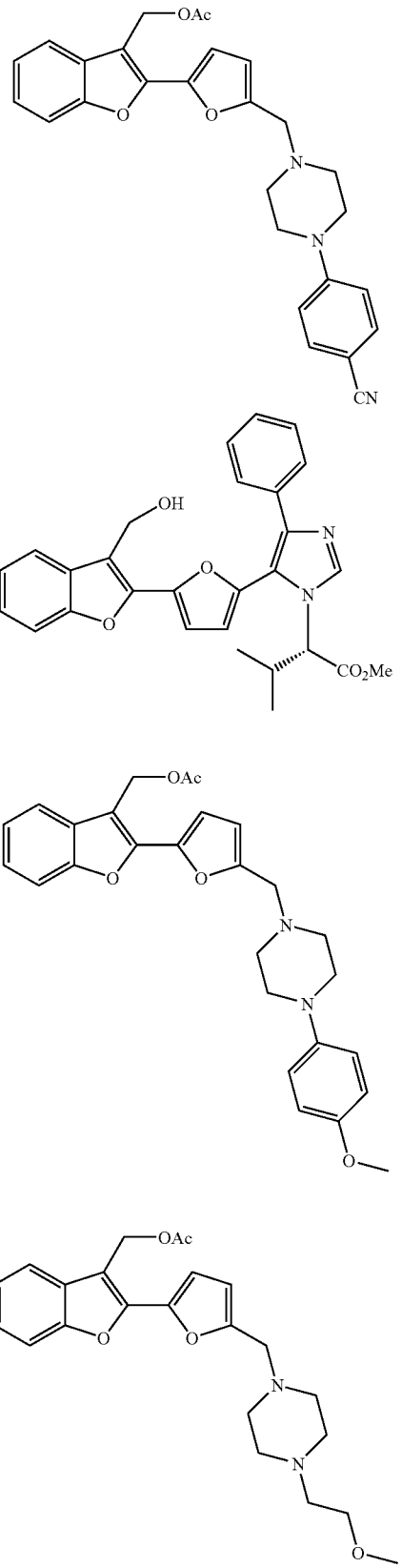

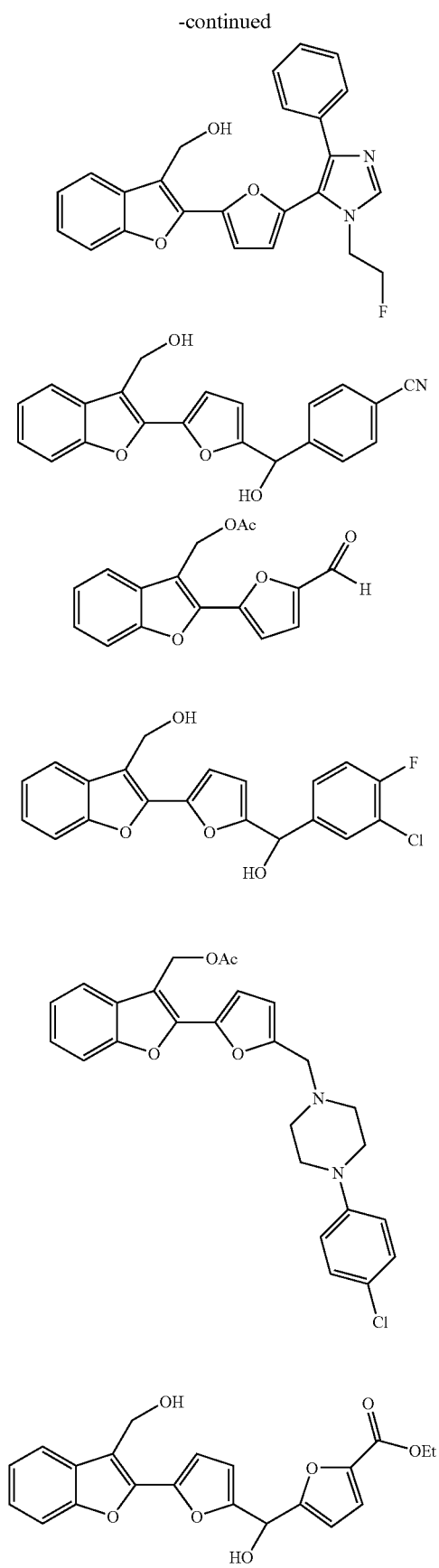
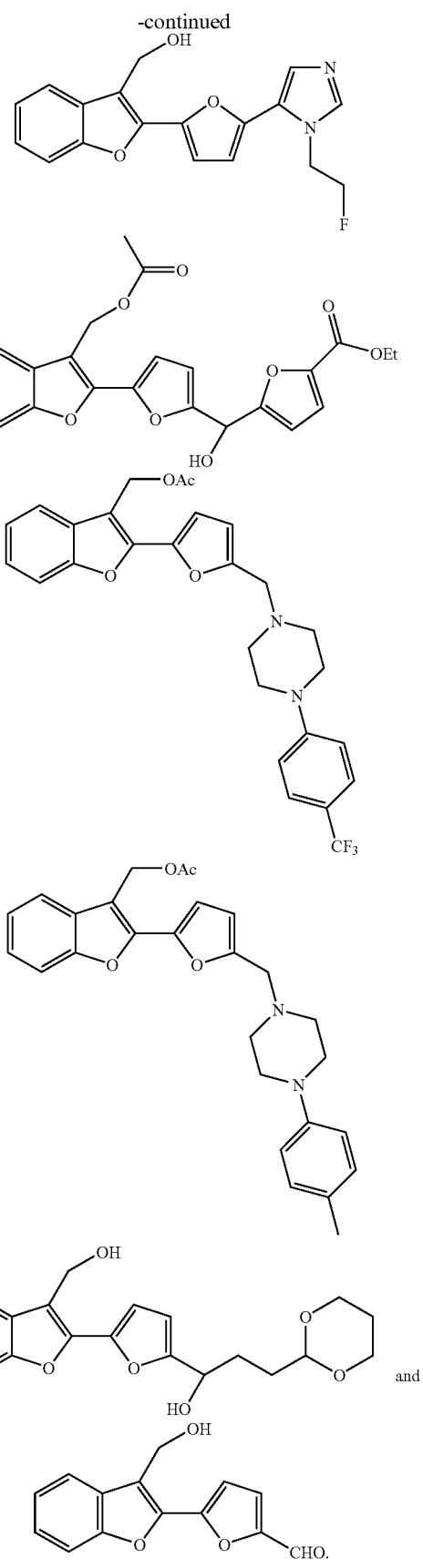

8. The compound of claim 7, wherein the label is a radioisotope selected from $^{3}H$, $^{11}C$, $^{14}C$, $^{18}F$, $^{32}P$, $^{35}S$, $^{123}I$, $^{125}I$, $^{131}I$, $^{51}Cr$, $^{36}Cl$, $^{57}Co$, $^{59}Fe$, $^{75}Se$, and $^{152}Eu$.

9. The compound of claim 7, wherein the wherein the label is a radioisotope selected from $^{3}H$, $^{11}C$, $^{14}C$, $^{18}F$, $^{32}P$, $^{35}S$, $^{123}I$, $^{125}I$, $^{131}I$, $^{36}Cl$, and $^{75}Se$.

10. The compound of claim 7, wherein the label is a paramagnetic particle selected from $^{157}Gd$, $^{55}Mn$, $^{162}Dy$, $^{52}Cr$, and $^{56}Fe$.

11. The compound of claim 7, wherein the label is an optical particle.

* * * * *

UNITED STATES PATENT AND TRADEMARK OFFICE
CERTIFICATE OF CORRECTION

PATENT NO. : 7,727,511 B2
APPLICATION NO. : 11/609129
DATED : June 1, 2010
INVENTOR(S) : Siclovan et al.

Page 1 of 3

It is certified that error appears in the above-identified patent and that said Letters Patent is hereby corrected as shown below:

On Page 2, in Item (56), under "OTHER PUBLICATIONS", in Column 1, Line 41, delete "βProtein Potentlyshibit" and insert -- β Protein Potently inhibit --, therefor.

On Page 2, in Item (56), under "OTHER PUBLICATIONS", in Column 2, Line 4, delete "Rakes" and insert -- Rakez --, therefor.

In FIG. 3, Sheet 3 of 9, delete "49(130nM) nM)" and insert -- 49 (130nM) --, therefor.

In Column 3, Line 42, delete "1 um× 1um" and insert -- 1μm×1μm --, therefor.

In Column 4, Line 55, delete "1 7-40" and insert -- 17-40 --, therefor.

In Column 11, in Table 1-continued, Lines 14-24, Structure 19a-20a, should read

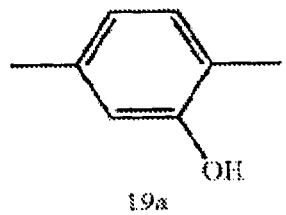

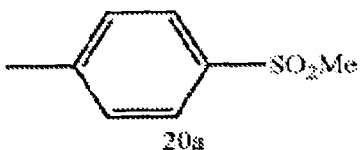

--                                --

Signed and Sealed this

Fifth Day of October, 2010

David J. Kappos
*Director of the United States Patent and Trademark Office*

In Column 19, in Table 2-continued, Lines 29-35, Structure 35b, should read

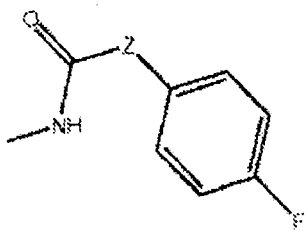

In Column 21, in Table 2, Lines 58-60, Structure 50b, should read

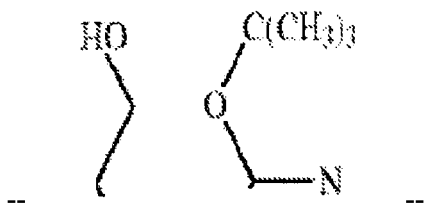

In Column 24, Line 58, delete "R3" and insert -- $R^3$ --, therefor.

In Column 26, in Table 3, Lines 33-38, Structure 8c, should read

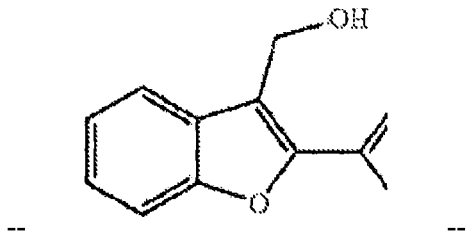

In Column 28, Line 11, delete "49b" and insert -- 16c --, therefor.

In Column 29, Line 23, delete "123I," and insert -- $^{123}$I, --, therefor.

In Column 29, Line 24, delete "125I," and insert -- $^{125}$I, --, therefor.

In Column 32, Line 13, delete "200 uM" and insert -- 200 μM --, therefor.

In Column 32, Line 53, delete "912ml)" and insert -- (12ml) --, therefor.

In Column 32, Line 66, delete "912ml" and insert -- (12ml) --, therefor.

In Column 35, Line 53, delete "500 uM" and insert -- 500 μM --, therefor.

In Column 35, Line 56, delete "210 uM" and insert -- 210 μM --, therefor.

CERTIFICATE OF CORRECTION (continued)
U.S. Pat. No. 7,727,511 B2

In Column 36, Line 3, delete "12 ug" and insert -- 12 μg --, therefor.

In Column 36, Line 10, delete "$^{and}$ $^3$H-37b" and insert -- and $^3$H-37b --, therefor.

In Column 36, Line 10, delete "12 ug" and insert -- 12 μg --, therefor.

In Column 36, Line 24, delete "50 uM" and insert -- 50 μM --, therefor.

In Column 36, Line 24, delete "10 uM and 50 uM" and insert -- 10 μM and 50 μM --, therefor.

In Column 39, Line 57, delete "beta" before "with".

In Column 40, Line 52, in Claim 3, delete "123I," and insert -- $^{123}$I, --, therefor.

In Column 40, Line 58, in Claim 6, delete "R3" and insert -- R$^3$ --, therefor.